United States Patent
Wang et al.

(10) Patent No.: US 6,570,029 B2
(45) Date of Patent: *May 27, 2003

(54) NO-FLOW REWORKABLE EPOXY UNDERFILLS FOR FLIP-CHIP APPLICATIONS

(75) Inventors: Lejun Wang, Atlanta, GA (US); Haiying Li, Atlanta, GA (US); Ching-Ping Wong, Berkley Lake, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/860,081

(22) Filed: May 17, 2001

(65) Prior Publication Data

US 2002/0035201 A1 Mar. 21, 2002

Related U.S. Application Data

(63) Continuation-in-part of application No. 09/820,549, filed on Mar. 29, 2001.
(60) Provisional application No. 60/193,356, filed on Mar. 29, 2000, and provisional application No. 60/205,590, filed on May 17, 2000.

(51) Int. Cl.$^7$ ............................................. C07D 303/02
(52) U.S. Cl. ...................................... 549/547; 549/546
(58) Field of Search ................................. 549/547, 546

(56) References Cited

U.S. PATENT DOCUMENTS

| | | | |
|---|---|---|---|
| 5,948,922 A | 9/1999 | Ober et al. | |
| 6,172,141 B1 | 1/2001 | Wong et al. | 523/455 |
| 6,180,696 B1 | 1/2001 | Wong et al. | 523/457 |

OTHER PUBLICATIONS

"Novel Thermally Reworkable Underfill Encapsulants for Flip–chip Applications," by Lejun Wang and C.P. Wong, pp. 92–100, 1998 Electronics Components and Technology Conference.

"Novel Thermally Reworkable Underfill Encapsulants for Flip–chip Applications," by Lejun Wang and C.P. Wong, The Second IEEE International Symposium on Polymeric Electronics Packaging, Oct. 24–28, 1999, Gothenburg, Sweden.

"Novel Thermally Reworkable Underfill Encapsulants for Flip–chip Applications," by Lejun Wang and C.P. Wong, IEEE Transactions on Advanced Packaging, pp. 46–53, vol. 22, No. 1, Feb. 1999.

"Syntheses and Characterizations of Thermally Reworkable Epoxy Resins, Part 1," by Lejun Wang and C.P. Wong, Journal of Polymer Science, Part A: Polymer Chemistry, pp. 2991–3001, vol. 37, 1999.

U.S. patent application Ser. No. 09/09/820,549, filed Mar. 29, 2001, entitled "Thermally Degradable Epoxy Underfills for Flip–Chip Applications."

*Primary Examiner*—Ba K. Trinh
(74) *Attorney, Agent, or Firm*—Troutman Sanders LLP; Todd Deveau; Ryan A. Schneider

(57) ABSTRACT

A no-flow reworkable epoxy underfill is provided for use in an electronic packaged system which incorporates an integrated circuit, an organic printed wire board, and at least one eutectic solder joint formed therebetween. An exemplary embodiment of the encapsulant includes: a cycloaliphatic epoxide; an organic hardener; a curing accelerator; and a fluxing agent wherein said cycloaliphatic epoxide includes a carbonate or carbamate group. The encapsulant can also include a filler, such as a silica filler. A method is also provided for forming the aforementioned reworkable epoxy underfills.

28 Claims, 14 Drawing Sheets

NO-FLOW REWORKABLE EPOXY UNDERFILLS FOR FLIP-CHIP APPLICATIONS

RELATED APPLICATIONS AND CLAIM OF BENEFIT AND PRIORITY

This application claims priority as a continuation-in-part of currently pending U.S. patent application Ser. No. 09/820,549, filed Mar. 29, 2001, now allowed which itself claims priority from U.S. Provisional Patent Application Ser. No. 60/193,356, filed Mar. 29, 2000. This application also claims priority from currently pending U.S. Provisional Patent Application No. 60/205,590, filed May 17, 2000.

FIELD OF THE INVENTION

This invention relates to thermally reworkable epoxy resin compositions, and more particularly to thermally reworkable carbamate or carbonate epoxide resin compositions which degrade at temperatures significantly lower than traditional cycloaliphatic epoxy resins.

BACKGROUND OF THE INVENTION

Modern electronics manufacturing relies upon two general techniques to attach electrical components, such as integrated circuit chips (IC's), resistors, capacitors and the like, to circuit boards. In the older, traditional reverse-mounting method, the components include wire leads which are extended through holes in the circuit board and soldered to connections on the back side of the circuit board. In recent years, the reverse-mounting method has been largely supplanted by the technique of surface-mounting, in which the components are soldered to the same side of the board to which they are mounted. Surface-mounting offers may advantages over the reverse-mounting method, including reduced assembly time, lower cost, and the ability to interconnect very small structures at a much higher density.

Integrated circuit (IC) chips usually have a large number of connecting leads in a very small area to support their high associated I/O requirements. Accordingly, surface-mounting techniques are well suited from the attachment of IC chips to circuit boards. One surface mounting technique which has grown in popularity in recent years is the technique known as "flip-chip" mounting. In the flip chip method, small solder bumps are positioned at locations on the surface of the circuit board and/or the underside of the chip wherein it is desired to form interconnections. The chip is mounted by placing it in contact with the circuit board and then heating it to cause the solder to reflow. Upon cooling, the solder hardens to attach the chip to the board and to create the appropriate electrical connections.

As initially practiced, the flip-chip technique oftentimes utilized relatively high cost materials, such as high lead solder and ceramic substrate. However, the desire to reduce costs has prompted the use of less expensive materials, such as in the flip-chip on board (FCOB) method, which typically utilizes eutectic solder and organic printed wiring board (PWB). While reducing material costs, the use of FCOB method has led to problems because of coefficient of thermal expansion mismatches between the IC chip and the organic substrate of the FCOB, particularly when large IC chips having a fine pitch and low profile solder joints are utilized. Due to the large coefficient of thermal explansion mismatch between silicon IC chips (2.5 ppm/° C.) and organic substrates, i.e., FR-4 PWB (18–24 ppm/° C.), temperature cycle excursions experienced by the FCOB can generate tremendous thermomechanical stress at the solder joints. Over time, these stresses can result in performance degradation of the interconnections which may degrade or incapacitate device performance.

One method developed to minimize the thermomechanical stresses on the solder joints has been to introduce an underfill material into the spaces or gaps remaining between an IC chip and substrate. The undefill is typically an adhesive, such as an epoxy resin, that serves to reinforce the physical and mechanical properties of the solder joints between the IC chip and the substrate. The underfill improves the fatigue life of the packaged system, and also serves to protect the chip and interconnections from corrosion by sealing the electrical interconnections of the IC chip from moisture. The use of an underfill can result in an improvement in fatigue life of ten to over one hundred fold, as compared to an un-encapsulated packaged system.

Cycloaliphatic epoxies, typically combined with organic acid anhydrides as a hardener, have commonly been used as underfills in flip-chip packaged systems. They offer the advantage of low viscosity prior to curing, and have acceptable adhesion properties after curing. Other epoxies such as bisphenol A or F type or naphthalene type have also been used in the underfill formulations. Silica powder has sometimes been utilized as a filler in underfill formulations in order to adjust the coefficient of thermal expansion of the underfill to match that of the solder. When the coefficients of thermal expansion of the solder and the underfill match there is much less movement and fatigue between the underside of the flip chip and the solder connections, further improving device lifetime.

By way of example, the material properties represented in Table 1 typically are exhibited by typical epoxy underfill compositions.

TABLE 1

Typical Underfill Properties

| | |
|---|---|
| Solids Content | 100% |
| Form | Single component, pre-mixed |
| Coefficient of Thermal Expansion ($\alpha_1$) | 22–27 ppm/° C. |
| Tg | >125° C. |
| Cure Temperature | <165° C. |
| Cure Time | <30 min. |
| Working Life (@ 25° C., visc. Double) | >16 hrs. |
| Viscosity (@ 25° C.) | <20 kcps |
| Filler Size | 95% < 15 $\mu$m |
| Filler Content | <70 wt % |
| Alpha Particle Emission | <0.005 counts/cm$^2$/hr. |
| Hardness (Shore D) | >85 |
| Modulus | 6–8 Gpa |
| Fracture Toughness | >1.3 Mpa-m$^{1/2}$ |
| Volume Resistivity (@ 25° C.) | >10$^{13}$ ohm-cm |
| Dielectric Constant (@ 25° C.) | <4.0 |
| Dissipation Factor (@ 25° C., 1 kHz) | <0.005 |
| Extractable Ions (e.g. Cl, Na, K, Fe, etc.) | <20 ppm total |
| Moisture Absorption (8 hrs. boiling water) | <0.25% |

While the use of underfills has presented a solution to the problem of the coefficient of thermal expansion mismatch between chip and circuit board, it has created new challenges for the electronics manufacturing process. The new manufacturing steps required to apply the underfill, and to bake the assembly to harden the underfill, substantially complicate and lengthen the manufacturing process. Accordingly, it would be desirable to simplify the underfill manufacturing process for flip chips.

One method of simplifying the manufacturing process has been to dispense the underfill before placing the flip chip into contact with the circuit board using a process known as "no-flow" underfill. In the no-flow underfill process, the underfill is applied directly to the underside of the chip and/or circuit board before alignment of the chip on the board. Thus, when using a no-flow process it is no longer necessary to use a low-viscosity underfill material that can flow into the thin space between the chip and the circuit board. This allows the use of higher viscosity underfill materials that are easier to handle and apply than the low viscosity underfills used in more traditional flow based flip-chip manufacturing. The manufacturing process is further simplified because the heating steps for soldering and curing the underfill can be combined, eliminating several manufacturing steps.

The no-flow underfill method requires that the underfill material be adapted to allow solder interconnects to form. Generally, a fluxing agent must be applied to the solder bumps and/or the circuit pads on the circuit board to aid in interconnect formation by removing oxidation from the circuit pads and solder bumps. Accordingly, fluxing agents have been included in some prior no-flow underfill compositions to facilitate solder joint formation.

An additional disadvantage to traditional flip chip methods has been that the use of an adhesive underfill can make it difficult, if not impossible, to disassemble the components when a defect is discovered after assembly of an electrical component. Because the solder assembly and underfill steps occur simultaneously during the heating process, it is difficult to test the electronic assembly until the assembly is complete. Thus, if a defect is discovered, the underfill has already hardened, making removal and disassembly impractical. This results in increased production costs due to the waste of otherwise usable components. An effective way to address this problem is to make the flip-chip devices reworkable under certain conditions.

One method of making a reworkable flip-chip device has been to incorporate a non-stick release coating on the boundary surface between a chip and a substrate. For example, U.S. Pat. No. 5,371,328 discloses a reworkable flip-chip type of circuit module using a non-stick release coating on all surfaces intermediate of the chip and the substrate. While this non-stick release coating may be suitable in some applications, it is likely that the use of such a release coating may reduce the adhesion of all the interfaces including those of the underfill to chip and underfill to substrate. These adhesions are important to the reliability of the flip chip interconnections. Accordingly, this approach is not ideal for use in flip-chip applications.

Another approach to providing a reworkable flip-chip interconnection is to use a reworkable underfill. Presently, the materials that are undergoing development for reworkable underfills can be classified into two categories: chemically reworkable underfills and thermally reworkable underfills.

Chemically reworkable underfills generally require the use of harsh acids and/or bases. For example, U.S. Pat. No. 5,560,934, issued to Afzali-Ardakani et al., discloses epoxy compositions that are soluble in an organic acid after curing. Utilizing relatively strong chemicals such as acids (or bases) during reworking, however, oftentimes leads to a messy, time-consuming rework process. Additionally, it has been found that the use of chemicals during the rework process typically makes localized repair of a packaged system difficult and, sometimes, impossible. Therefore, it is believed that use of a thermal rework process would avoid these problems and offer the possibility of a quick, clean, and localized rework process.

U.S. Pat. No. 5,659,203, issued to Call et al., discloses a reworkable flip-chip module utilizing a specially defined thermoplastic resin as an encapsulant. The thermoplastic resin, such as polysulfone, polyetherimide, etc., possesses a high glass transition temperature (Tg), e.g., 120° C.<Tg<220° C., and must be either dissolved in a solvent or heated above its melting point during the encapsulation process. Therefore, use of these thermoplastic resins as encapsulants for FCOB applications may be undesirable, since such applications typically require an underfill which is free of solvent and in liquid form during the encapsulation process, and typically require keeping the packaged system at lower temperatures in order to maintain the integrity of the eutectic solder which is utilized with the organic PWB.

U.S. Pat. Nos. 6,197,122 and 5,948,922, issued to Ober et al., disclose thermally reworkable underfill formulations based on thermally decomposable epoxies containing secondary or tertiary oxycarbonyl (ester) moieties. However, secondary or tertiary oxycarbonyl moieties typically can easily be cleaved by weak acid or base, and are sensitive to moisture. Also the epoxies containing secondary or tertiary oxycarbonyls typically have higher moisture uptake than a standard epoxies. All these factors tend to indicate that epoxies containing secondary or tertiary oxycarbonyl moieties might not be suitable for underfill applications where high reliability is required.

Thus, it can be seen that none of the prior art methods are ideally suited for use as a no-flow underfill to bond chip and substrate to allow fast and efficient assembly and rework of FCOB devices without sacrificing the reliability of the devices. Therefore, it is desirable to provide a no-flow underfill composition that has useful fluxing properties and which will not negatively affect the overall performance of the assembly, while still allowing cost effective and efficient rework.

SUMMARY OF THE INVENTION

Accordingly, it is an object of the present invention to provide a polymeric composition that has mechanical and fluxing properties suited to use as a no-flow underfill while also offering thermal reworkability. The present invention is focused on epoxy base materials because epoxy base materials have desirable properties for use as an underfill and are the only materials that have been proven to provide flip-chip devices with acceptable reliability.

Most epoxy materials are thermosetting compositions and are difficult or impossible to remove after curing. The present invention overcomes this limitation by developing new diepoxides that contain thermally degradable groups within their structures and using these new diepoxides in the epoxy formulations to make the thermoset network degradable at a desired temperature. This makes the new epoxy formulations reworkable. Moreover, these thermally degradable groups have good properties such as high moisture resistance, high chemical resistance and low moisture uptake so that they are suitable for underfill application. This improvement is advantageous in flip-chip application of epoxy compositions where epoxy materials are used as the underfill to reinforce the solder joints. Removal of the epoxy allows replacement of defective devices, saving the cost of discarding other valuable components in a microelectronic assembly.

There are two ways of developing reworkable epoxy base materials. One is to develop new epoxies that decompose at rework temperature. The other is to develop additives to add into the existing epoxy formulations that have previously been found suitable for use as underfill encapsulants. The present invention focuses on the first category and uses thermally degradable epoxies containing integral thermally cleavable groups that decompose at rework temperatures. The second category is the subject of U.S. Pat. No. 6,172,141.

The thermally cleavable groups of the present invention have been selected to meet the following criteria:
1. The cleavable groups should be sufficiently stable to permit the epoxy network to perform its function in a specific application;
2. The cleavable groups should be inert to the curing reaction of the epoxy network;
3. The cleavable groups should not adversely affect the overall properties of the epoxy network;
4. The cleavable groups should decompose quickly at elevated temperature so that they break down the structure of the epoxy network, leading to its easy rework.
5. The link should be stable in the environment to which the cured epoxy will be exposed.
6. The synthesis of the epoxides containing the cleavable link should be simple, with high yield, and cost effective.

The present invention discloses carbonate and carbamate epoxides which have been found to meet the above criteria. After introduction into the epoxy structure, the carbamate and carbonate groups do not significantly interfere with epoxy curing, nor do they adversely affect epoxy properties including Tg, modulus, CTE, adhesion. However, the existence of these groups inside the epoxy structure reduces the epoxy decomposition temperature from 350° C. to as low as 200° C. Optimal rework temperatures for flip-chip devices are generally between 200° C. and 250° C. because the eutectic solder reflow temperature is within this temperature region. Therefore, these two groups may be suitable for use in applications needing an epoxy which is reworkable around solder reflow temperature.

More particularly, the present invention is directed to a thermally reworkable no-flow epoxy composition for encapsulating and protecting an electronic device or assembly. The thermally reworkable epoxy composition includes the cured reaction product of: a cycloaliphatic epoxide containing either a carbonate or a carbamate group; an organic hardener; a curing accelerator; and a fluxing agent. The present invention is also directed to a method of protecting, encapsulating, reinforcing, assembling, or fabricating a device or a chemical product with a cured epoxy composition which is thermally reworkable, wherein the epoxy composition includes the reaction product of: a thermally degradable cycloaliphatic epoxide; an organic hardener; a curing accelerator and a fluxing agent.

DETAILED DESCRIPTION

Figure 1:
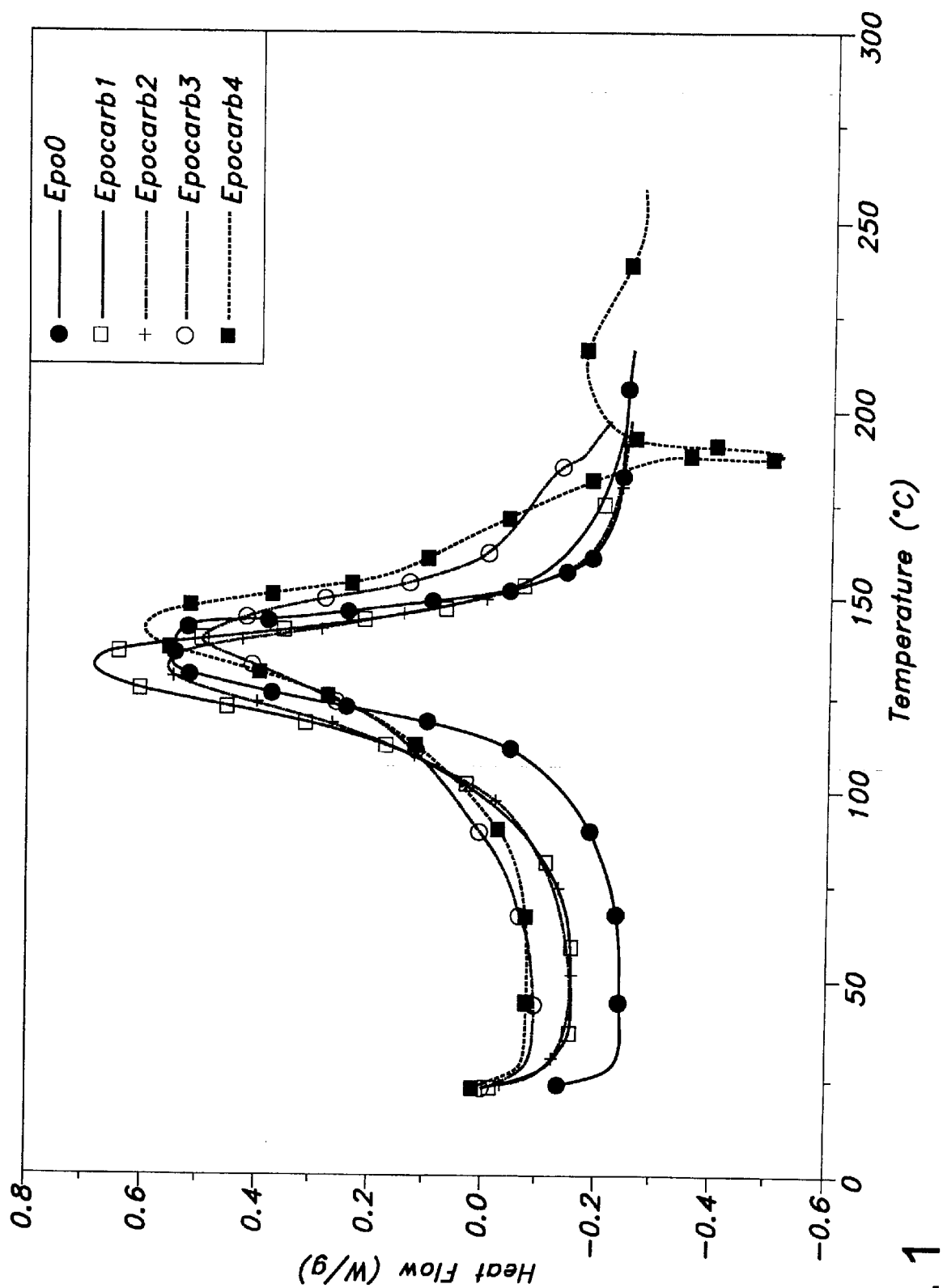
FIG. 1 is a graph illustrating DCS scan data for Epo0 and Epocarb1 through Epocarb4.

The following illustrative embodiments describe the thermally degradable no-flow epoxy underfills of the present invention and are provided for illustrative purposes and are not meant as limiting the invention.

Generally, the no-flow reworkable epoxy compositions of the present invention include: a cycloaliphatic epoxide containing either carbonate or carbamate group; an organic hardener; a curing accelerator; and a fluxing agent. The compositions of the present invention may also include: a silane coupling agent; a rubber toughening agent; and/or silica filler. Preferably the epoxy compositions of the present invention include to 50 parts by weight cycloaliphatic epoxide: 20.0 to 80.0 parts organic hardener; 0.05 to 1.0 parts curing accelerator; and 1 to 10 parts fluxing agent. More preferably, the epoxy compositions of the present invention include to 50 parts by weight cycloaliphatic epoxide: 40.0 to 60.0 parts organic hardener; 0.1 to 0.5 parts curing accelerator; and 2.0 to 5.0 parts fluxing agent.

In accordance with the exemplary embodiments of the present invention, the cycloaliphatic epoxide used can contain either a carbonate or a carbamate group. The structures of several thermally degradable epoxy resins containing a carbonate group, Carb1 through Carb4, are shown below in accordance with the present invention. Among these epoxides, Carb3 is a monoepoxide while all others are diepoxides.

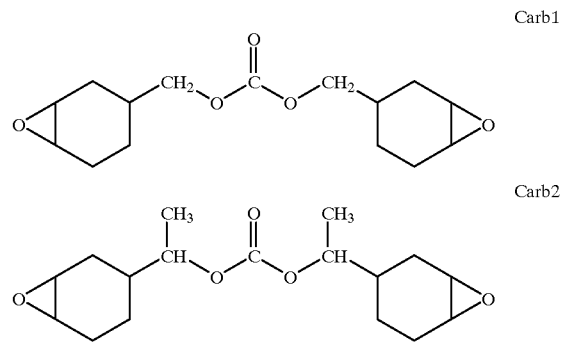

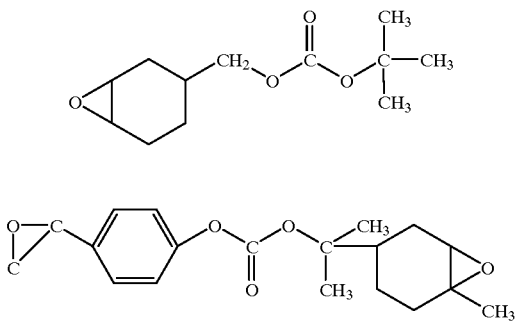

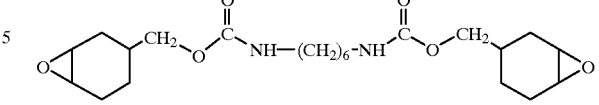

Likewise, the structures of several thermally degradable diepoxides containing a carbamate (urethane) group, Uret1 through Uret7 are illustrated below in accordance with the present invention.

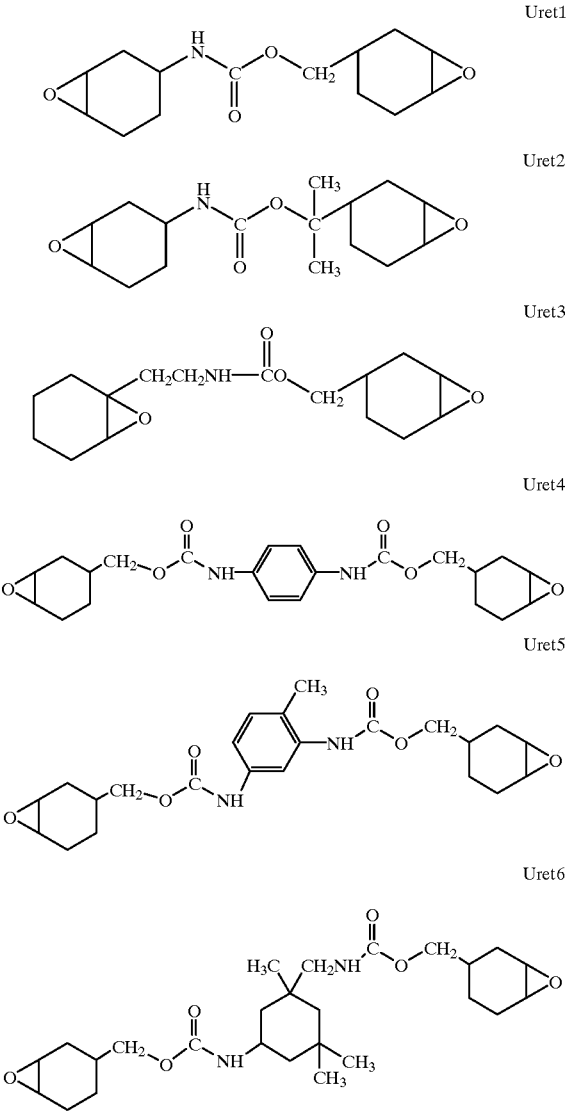

The properties of several of the compounds are set forth in more detail in the following sections.

EXAMPLE 1

This example discloses the synthesis of Carb1.

1) Synthesis of Di-cyclohex-3-enylmethyl Carbonate

Triphosgene (4.40 g) was dissolved in methylene chloride (80 ml), and added slowly to the methylene chloride solution (200 ml) of 3-cyclohexene-1-methanol (9.2 ml), and pyridine (16 ml). The addition was finished in 1 hr. Then the mixture was kept refluxing for 7 hrs, washed with 0.5 M HCl solution (100 ml), 5% sodium bisulfite (500 ml), 2.5% sodium bicarbonate (500 ml), dried with magnesium sulfate, filtered and evaporated to give a 76% yield of liquid product identified by IR and NMR. IR (neat): 3024, 2916, 2839, 1747, 1402, 1259, 962, 751, 656 cm$^{-1}$. $^1$H NMR (CDCl$_3$): δ 5.6 (s, 4H, =CH), 4.0 (d, 4H, CH$_2$O), 2.2–1.9 (complex m, 8H, CH$_2$), 1.8–1.6 (complex m, 4H, CH$_2$), 1.4–1.2 (complex m, 2H, CH) ppm.

2) Synthesis of Di-3,4-epoxycyclohexylmethyl Carbonate (Carb1)

Di-cyclohex-3-enylmethyl carbonate (9.80 g) was dissolved in methylene chloride (75 ml) and acetone (75 ml) in a four-neck flask equipped with a mechanical stirrer, a pH meter and two adding funnels. A pH 7.5/0.1 M phosphate buffer (50 ml) and an 18-crown-6 crown ether (0.75 g) were then added into the mixture. The mixture was stirred in an ice bath to reduce its temperature to below 5° C. before the start of the simultaneous addition of a 0.5 M KOH aqueous solution and a solution of OXONE (potassium peroxymonosulfate, 36.9 g in 200 ml water containing 0.05 g of ethylenediaminetetraacetic acid). Rapid stirring was continued throughout the addition, and the temperature was kept below 5° C. all the time. The relative addition speed of the two solutions was adjusted to keep the pH of the reaction mixture in between 7 and 8. Addition of the OXONE solution was completed in 2 hrs, followed by additional 3.5 hrs of stirring, and the pH was maintained in the above range by a slow addition of 1.0 M KOH. Then the organic phase was isolated, dried with magnesium sulfate, filtered and evaporated to give a 90% yield of the liquid diepoxide identified by IR and NMR. IR (neat): 2930, 1744, 1403, 1259, 960, 790 cm$^{-1}$. $^1$H NMR (CDCl$_3$, in ppm): δ 4.0–3.8 (m, 4H, CH$_2$O), 3.1 (d, 4H, CH on epoxide ring), 2.1–0.9 (complex m, 14H, CH$_2$+CH) ppm. The synthesis scheme for Carb1 is diagrammed below:

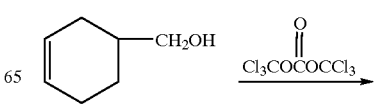

9

-continued

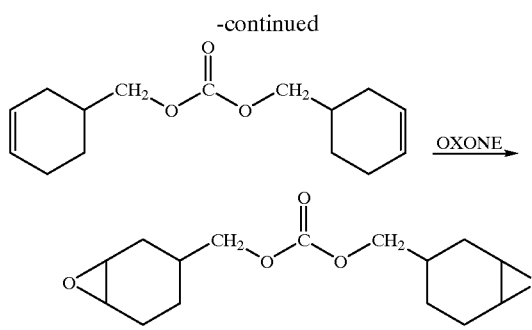

OXONE→

EXAMPLE 2

This example discloses the synthesis of Carb2
1) Synthesis of Di-1-(3-cyclohexenyl)ethyl Carbonate The same procedure as of di-cyclohex-3-enylmethyl carbonate was followed except that the alcohol used is 1-(3-cyclohexenyl)-1-ethanol instead of 3-cyclohexene-1-methanol. The yield was 80%. Its structure was identified by IR and NMR. IR (neat): 3024, 2918, 2839, 1739, 1438, 1378, 1263, 1141, 1035, 920, 658 cm$^{-1}$. $^1$H NMR (CDCl$_3$): δ 5.6 (s, 4H, =CH), 4.6 (m, 2H, CHO), 2.2–1.9 (complex m, 8H, CH$_2$), 1.8–1.6 (complex m, 4H, CH$_2$), 1.4–1.2 (complex, 8H, CH$_3$+CH) ppm.

2) Synthesis of Di-1-(3,4-epoxycyclohexenyl)ethyl Carbonate (Carb2)

Following the same epoxidation procedure as for CARB1, a liquid with 89% yield was obtained which was identified by IR and NMR. IR (neat): 2984, 2938, 1736, 1436, 1363, 1268, 1058, 1030, 927, 794, 736 cm$^{-1}$. $^1$H NMR (CDCl$_3$): δ 4.6 (m, 2H, CHO), 3.1 (d, 4H, CH on epoxide ring), 2.1–0.9 (complex m, 20H, CH$_3$+CH$_2$+CH) ppm.

EXAMPLE 3

This example discloses the synthesis of Carb3.
1) Synthesis of Cyclohex-3-enylmethyl t-butyl Carbonate Triphosgene (4.40 g) was dissolved in the methylene chloride solution (50 ml) and cooled in an ice bath. To this solution a methylene chloride solution (50 ml) of 3-cyclohexene-1-methanol (4.6 ml) and pyridine (8 ml) was slowly added. The addition was finished in 1 hr. Then the mixture was kept stirring for 4 hours in the ice bath during which 3-cyclohexene-1-methyl chloroformate was formed.

To the above mixture a methylene chloride solution (50 ml) of 2-methyl-2-propanol (3.0 ml) and pyridine (8 ml) was then added in one protion. The mixture was then stirred at room temperature for overnight. It was washed with 0.5 M HCl solution (100 ml), 5% sodium bisulfite (500 ml), 2.5% sodium bicarbonate (500 ml), and dried with magnesium sulfate. The organic phase was then concentrated and purified with column chromatography on silica gel with methylene chloride to give a 47% yield of the product as a colorless liquid identified by IR and NMR. IR (neat): 3025, 2918, 2840, 1743, 1396, 1259, 1165, 961, 858, 739, 656 cm$^{-1}$. $^1$H NMR (CDCl$_3$): δ 5.6 (s, 2H, =CH), 4.0–3.8 (d, 2H, CH$_2$O), 2.2–1.2 (complex m, 7H, CH$_2$+CH), 1.4 (s, 9H, CH$_3$) ppm.

2) Synthesis of 3,4-epoxycyclohexylmethyl t-butyl Carbonate (Carb3)

Following the same epoxidation procedure as for Carb1, a liquid with 89% yield was obtained which was identified by IR and NMR. IR (neat): 2982, 2933, 1743, 1255, 1163, 859, 790 cm$^{-1}$. $^1$H NMR (CDCl$_3$): δ 4.0–3.8 (m, 2H, CH$_2$O), 3.2 (d, 2H, CH on epoxide ring), 2.2–1.0 (complex m, 7H,

10

CH$_2$+CH), 1.4 (s, 9H, CH$_3$) ppm. The synthesis scheme for Carb3 is diagrammed below:

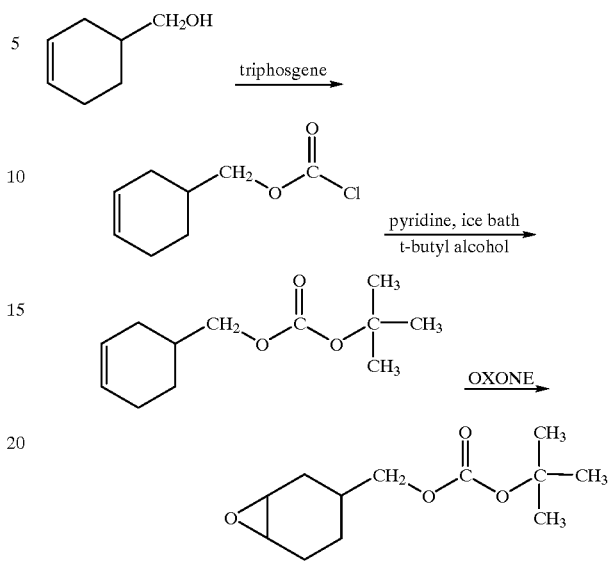

EXAMPLE 4

This example discloses the synthesis of Carb4.
1) Synthesis of 4-vinylphenyl 2-(3-methyl-3-cyclohexenyl)-2-propyl Carbonate In a 250 ml three-necked round-bottomed flask equipped with a dropping funnel, a nitrogen bubblier and a magnetic stirring bar, triphosgene (1.0 g) in methylene chloride solution (50 ml) was placed. The temperature was lowed to 0° C. with ice bath. A methylene chloride solution (50 ml) of 4-vinyl phenol (1.2 g) and pyridine (8 ml) was added dropwise over 30 min from the dropping funnel. The resulting mixture was stirred at 0–5° C. for 8 hr and the reaction proceeding was monitored with TLC till all 4-vinyl phenol was converted to 4-vinylphenyl chloroformate.

The resulting mixture above was used directly without treatment and the same reaction system was used continuously. The dropping funnel on the flask was charged of α-terpineol (7.7 g) and quinoline (6.5 g). The formed solution was added dropwise to the reaction system at room temperature over vigorous stirring. The mixture was stirred over night and a white salt gradually precipitated. The salt was separated and the organic phase was washed with 2 N HCl and water until all pyridine and quinoline were neutralized and washed out. The organic phase was separated, washed with sodium bicarbonate and sodium bisulfite solution, and then dried over anhydrous magnesium sulfate. The column chromatography of the products on silica gel with 10:1 hexane/ethyl acetate gave 32% yield of the product as a colorless viscous liquid. FT-IR (neat): 2925, 1757, 1508, 1446, 1376, 1264, 1214, 1157, 1123, 1018, 990, 903, 840, 809 cm$^{-1}$. $^1$H NMR (CDCl$_3$): δ 7.40 (d, 2H, aromatic), 7.12 (d, 2H, aromatic), 6.69 (dd, 1H, =CH, aromatic), 5.70 (dd, 1H, =CH$_2$), 5.38 (m, 1H, =CH), 5.24 (dd, 1H, =CH$_2$), 2.19–1.83 (m, 6H, CH$_2$), 1.66 (s, 3H, CH$_3$) 1.54 (s, 3H, CH$_3$), 1.51 (s, 3H, CH$_3$), 1.44–1.25 (m, 1H, CH) ppm.

2) Synthesis of 4-epoxyethyllphenyl 2-(3-methyl-3,4-epoxycyclohexyl)-2-propyl Carbonate (Carb4)

Following the same epoxidation procedure as for Carb1, a viscous colorless liquid with 89% yield was obtained.

FT-IR (neat): 2925, 1757, 1508, 1446, 1376, 1264, 1214, 1157, 1123, 1018, 990, 903, 840, 809 cm$^{-1}$. $^1$H NMR (CDCl$_3$): δ 7.40 (d, 2H, aromatic), 7.11 (d, 2H, aromatic), 3.70 (dd, 1H, CO), 3.14 (t, 1H, CO), 2.89 (d, 1H, CHO), 2.81 (d, 1H, CHO), 2.12–1.44 (m, 6H, CH$_2$), 1.62 (s, 3H, 1CH$_3$), 1.52 (s, 3H, 1CH$_3$), 1.50 (s, 6H, 2CH$_3$), 1.42–1.20 (m, 1H, CH) ppm. The synthesis scheme for Carb4 is diagrammed below:

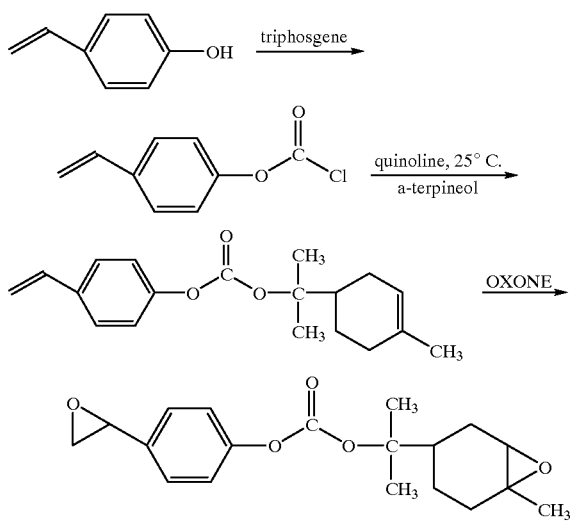

EXAMPLE 5

This example discloses Epoxide Equivalent Weights (EEWs) of Carb1 through Carb4.

Their EEWs were measured according to ASTM titration procedure D1652-90. Table 1 shows their theoretical and measured EEW values. It can be seen that the measured values were generally in good agreement with the theoretical values.

TABLE 1

EEWs of Carb1 through Carb4

| Sample | EEW (g/mol.) | |
| --- | --- | --- |
| | Theoretical | Measured |
| Carb1 | 141 | 157 |
| Carb2 | 153 | 165 |
| Carb3 | 228 | 235 |
| Carb4 | 165.5 | 207 |

EXAMPLE 6

This example discloses the synthesis of Uret1.
1) Synthesis of 3-cyclohexene-1-isocyanate Sodium azide (8.00 g) was dissolved in water (20 ml) in a 250 ml 3-neck flask. The flask was put in an ice path to control the temperature around 0° C. While the aqueous solution was stirred, benzene solution (100 ml) of 3-cyclohexene-1-carbonyl chloride (8.70 g) was added in dropwise. The addition was completed in about 2 hrs. The mixture was stirred for another 4 hrs, with the temperature around 0° C. Then the aqueous phase was separated from the organic phase, extracted with benzene (50 ml). The two organic phases were combined and dried with magnesium sulfate for several hours. The dried benzene solution was then heated to 50° C. in a 250 ml flask in a water bath for several hours until no gas was emitted. The obtained benzene solution of isocyanate was directly used for later synthesis.

2) Synthesis of 3-cyclohexen-1-isocyanate cyclohex-3-enylmethyl Carbamate

A Benzene solution of isocyanate (65 ml), 3-cyclohexene-1-methanol (3.50 ml), and pyridine (3.00 ml) were mixed in a 250 ml 3-neck flask, refluxing for 6 hrs. Then water (100 ml) was added in. The mixture was refluxed for another 1 hr. The mixture was then washed with 0.05 M HCl three times, followed by water three times. The organic phase was then separated from the water phase and dried with magnesium sulfate for several hours before benzene was removed by rotary evaporation to give a liquid. It was purified by column chromatography with 60% yield. This liquid material was identified by its spectra. IR (neat, in cm$^{-1}$): 3340, 3025, 2915, 2845, 2255, 1700, 1525, 1440, 1305, 1270, 1235, 1140, 1050, 975, 925, 875, 780, 750, 720, 655. $^1$H NMR (CDCl$_3$, in ppm): δ 7.1 (d, m, 1H), 5.7–5.5 (d, s, 4H), 3.8 (d, s, 2H), 3.5 (s, m, 1H), 3.3 (d, s, 2H), 2.2–1.6 (complex, s, 9H), 1.5–1.1 (complex, m, 2H). Its purity was verified by TLC.

3) Synthesis of 3,4-epoxycyclohexyl-1-isocyanate 3,4-epoxycyclohexylmethyl Carbamate (Uret1)

3-cyclohexen-1-isocyanate cyclohex-3-enylmethyl carbamate (9.80 g) was dissolved in methylene chloride (75 ml) and acetone (75 ml) in a four-neck flask equipped with a mechanical stirrer, a pH meter and two adding funnels. A pH 7.5/0.1 M phosphate buffer (50 ml) and an 18-crown-6 crown ether (0.75 g) were then added into the mixture. The mixture was stirred in an ice bath to reduce its temperature to below 5° C. before the start of the simultaneous addition of a 0.5 M KOH aqueous solution and a solution of OXONE (potassium peroxymonosulfate, 36.9 g in 200 ml water containing 0.05 g of ethylenediaminetetraacetic acid). Rapid stirring was continued throughout the addition, and the temperature was kept below 5° C. all the time. The relative addition speed of the two solutions was adjusted to keep the pH of the reaction mixture in between 7 and 8. Addition of the OXONE solution was completed in 2 hrs, followed by additional 3.5 hrs of stirring, and the pH was maintained in the above range by a slow addition of 1.0 M KOH. Then the organic phase was isolated, dried with magnesium sulfate, filtered and evaporated to give a 92% yield of the liquid diepoxide identified by IR and NMR. IR (neat, in cm$^{-1}$): 3340, 2940, 1700, 1530, 1435, 1310, 1255, 1225, 1045, 800. $^1$H NMR (CDCl$_3$, in ppm): δ 5.0 (d, m, 1H), 4.6 (s, m, 1H), 3.8 (m, m, 2H), 3.6 (s, m, 1H), 3.2–3.0 (m, s, 4H), 2.4–0.9 (complex, 12H). The synthesis scheme for Uret1 is diagrammed below:

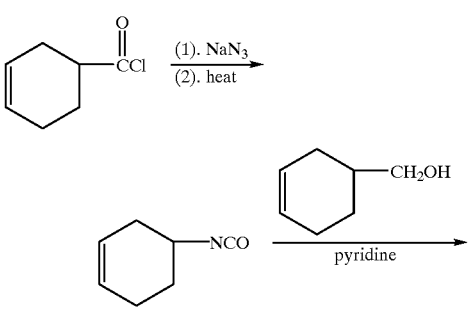

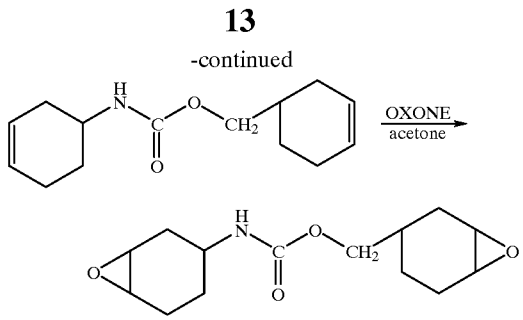

EXAMPLE 7

This example discloses the synthesis of Uret2.
1) Synthesis of 3-cyclohexen-1-isocyanate 2-(3-cyclohexenyl)-2-propyl Carbamate 3-cyclohexen-1-isocyanate 2-(3-cyclohexenyl)-2-propyl carbamate was obtained by following the same procedure as for 3-cyclohexen-1-isocyanate cyclohex-3-enylmethyl carbamate except 2-(3-cyclohexenyl)-2-propanol was used to replace 3-cyclohexen-1-methanol. It was purified by column chromatography with 44% yield. Spectra confirmed the structure. IR (neat, in cm$^{-1}$): 3333, 3025, 2928, 2825, 1620, 1531, 1438, 650. $^1$H NMR (CDCl$_3$, in ppm): δ 5.7–5.5 (d, s, 4H), 3.7 (s, m, 1H), 2.4–1.3 (complex, 14H), 1.2 (m, s, 6H). Its purity was verified by TLC.

2) Synthesis of 3,4-epoxycyclohexyl-1-isocyanate 2-(3,4-epoxycyclohexyl)-2-propyl Carbamate (Uret2)

Following the same procedure as for Uret1, a 95% yield of Uret2 was obtained and identified by IR and NMR. IR (neat, in cm$^{-1}$): 3345, 2974, 2925, 1700, 1525, 1358, 802. $^1$H NMR (CDCl$_3$, in ppm): δ 3.6 (s, m, 1H), 3.3–3.0 (d, s, 4H), 2.4–1.3 (complex, 14H), 1.2 (m, s, 6H).

EXAMPLE 8

This example discloses the synthesis of Uret3.
1) Synthesis of Cyclohex-3-enylmethyl Chloroformate 2-(1-cyclohexenyl)ethyl Carbamate To the methylene chloride solution (40 ml) of triphosgene (2.20 g), a methylene chloride solution (60 ml) of 3-cyclohexen-1-methanol (2.40 ml) and pyridine (3.50 ml) was slowly added. The addition was completed in 1 hr. The mixture was then refluxed for 1 hour, cooled down to room temperature, and stirred for another 2 hrs. A yellowish green solution was obtained.

Methylene chloride solution (50 ml) of 2-(1-cyclohexenyl) ethylamine (2.70 ml) and pyridine (3.50 ml) was added into the above mentioned yellowish green solution in one portion. Instantly, the color of the mixture changed from yellowish green to pink. The mixture was refluxed for 2 hrs. Then it was washed with 0.5 M HCl, water, 5% sodium bisulfite solution, 2.5% sodium bicarbonate solution, and saturated sodium chloride solution before it was dried with magnesium sulfate, filtered, and evaporated to give a 80% yield of liquid. Its structure was confirmed by the IR and NMR spectra. IR (neat, in cm$^{-1}$): 3403, 3341, 3019, 3017, 2845, 1718, 1515, 1439, 1254, 742, 653. $^1$H NMR (CDCl$_3$, in ppm): δ 5.6 (t, s, 2H), 5.5–5.3 (m, m, 1H), 4.0(m, m, 2H), 3.5 (d, s, 2H), 3.3 (d, m, 1H), 2.2–1.2 (complex, 17H). Its purity was verified by TLC.

1) Synthesis of 3,4-epoxycyclohexylmethyl 2-(1,2-epoxycyclohexyl)ethyl Carbamate (Uret3)

Following the same procedure as for Uret1, an 89% yield of Uret3 in the form of a liquid was obtained and identified by IR and NMR. IR (neat, in cm$^{-1}$): 3345, 2932, 1708, 1520, 1436, 1252, 735. $^1$H NMR (CDCl$_3$, in ppm): δ 5.1 (s, w, 1H), 3.9–3.7 (m, m, 2H), 3.4–2.9 (complex, 6H), 2.2–0.9 (complex, 16H). The synthesis scheme for Uret3 is diagrammed below:

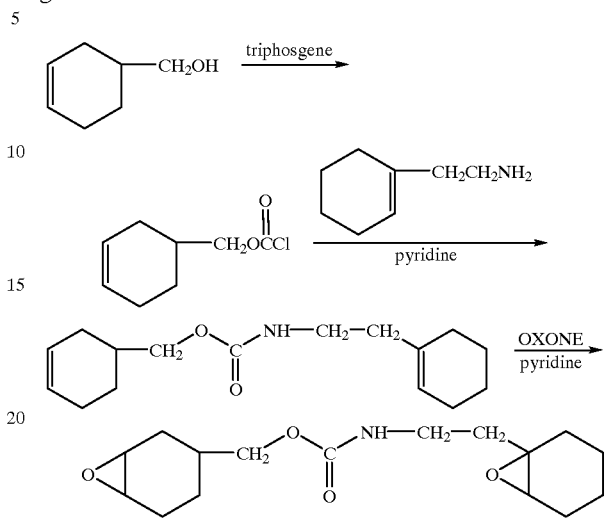

EXAMPLE 9

This example discloses the synthesis of Uret4.
1) Synthesis of Phenylene-1,4-diisocyanate Bis-(cyclohex-3-enylmethyl) Dicarbamate To a pyridine solution (40 ml) of 3-cyclohexene-1-methanol (12.00 ml) in the 500 ml 3-neck flask equipped with a temperature controller, a condenser, and an adding funnel, an acetone solution (150 ml) of phenylene-1,4-diisocyanate (12.00 g) was slowly added in, while the mixture was kept stirring. The addition was completed in 1 hr, followed by refluxing for 6 hrs. Then acetone and pyridine were evaporated out to give a raw solid product with 79% yield. The raw solid was washed with 0.5 M HCl and water several times, before it was dried in vacuum. Spectra confirmed the structure. IR (KBr pellet, in cm$^{-1}$): 3329, 3025, 2948, 2850, 1700, 1539, 1413, 1304, 1239, 1067, 649. $^1$H NMR (CDCl$_3$, in ppm): δ 7.3 (s, s, 4H), 6.7 (s, m, 2H), 5.7 (s, s, 4H), 4.0 (d, s, 4H), 2.2–1.2 (complex, 14H). Its purity was verified by TLC.

2) Synthesis of Phenylene-1,4-diisocyanate Bis-(3,4-epoxycyclohexylmethyl) Dicarbamate (Uret4)

Following the same procedure as for Uret1, solid Uret4 with yield 81% was obtained and identified by IR and NMR. IR (KBr pellet, in cm$^{-1}$): 3330, 2943, 1702, 1542, 1423, 1305, 1228, 1069, 817, 853. $^1$H NMR (CDCl$_3$, in ppm): δ 7.3 (s, s, 4H), 6.5 (s, m, 2H), 3.9 (m, s, 4H), 3.2 (d, s, 4H), 2.2–1.0 (complex, 14H).

EXAMPLE 10

This example discloses the synthesis of Uret5.
1) Synthesis of Tolylene-2,4-diisocyanate Bis-(cyclohex-3-enylmethyl) Dicarbamate Following the same procedure as for phenylene-1,4-diisocyanate bis-(cyclohex-3-enylmethyl) dicarbamate except that an acetone solution of phenylene-1,4-diisocyanate was replaced by tolylene-2,4-diisocyanate, solid tolylene-2,4-diisocyanate bis-(cyclohex-3-enylmethyl) dicarbamate was obtained with 78% yield, and was identified by IR and NMR. IR (KBr pellet, in cm$^{-1}$): 3329, 3015, 2900, 2813, 1702, 1542, 1413, 1304, 1230, 1067, 649. $^1$H NMR (CDCl$_3$, in ppm): δ 7.2–7.0 (complex, 3H), 6.6–6.4 (d, m, 2H), 5.6 (s, s, 4H), 4.0 (m, s, 4H), 2.3–1.2 (complex, 17H). Its purity was verified by TLC.

2) Synthesis of Tolylene-2,4-diisocyanate Bis-(3,4-epoxycyclohexylmethyl) Dicarbamate (Uret5)

Following the same procedure as for Uret1, solid Uret5 with yield 85% was obtained and identified by IR and NMR. IR (KBr pellet, in cm$^{-1}$): 3303, 2936, 1730, 1599, 1532, 1416, 1224, 1056. $^1$H NMR (CDCl$_3$, in ppm): δ 7.2–7.0 (complex, 3H), 6.6–6.4 (d, m, 2H), 3.9 (m, s, 4H), 3.1 (s, s, 4H), 2.3–1.2 (complex, 17H).

EXAMPLE 11

This example discloses the synthesis of Uret6.

1) Synthesis of Isophorone Diisocyanate Bis-(cyclohex-3-enylmethyl) Dicarbamate

Isophorone diisocyanate bis-(cyclohex-3-enylmethyl) dicarbamate solid was obtained with 80% yield by following the same procedure as for phenylene-1,4-diisocyanate bis-(cyclohex-3-enylmethyl) dicarbamate except that the acetone solution of phenylene-1,4-diisocyanate was replaced by isophorone diisocyanate. IR and NMR spectra confirmed the structure. IR (KBr pellet, in cm$^{-1}$): 3343, 3025, 2938, 1684, 1529, 1257, 1222, 1140, 643. $^1$H NMR (CDCl$_3$, in ppm): δ 5.6 (s, s, 4H), 4.6 (s, m, 2H), 3.9 (d, s, 4H), 3.1 (s, s, 3H), 2.1–1.2 (complex, 29H). Its purity was verified by TLC.

2) Synthesis of Isophorone Diisocyanate Bis-(3,4-epoxycyclohexylmethyl) Dicarbamate (Uret6)

Uret6 solid was obtained with 90% yield by following the same procedure as for Uret1. Its structure was identified by IR and NMR. IR (KBr pellet, in cm$^{-1}$): 3344, 2937, 1683, 1531, 1257, 1140, 1050. $^1$H NMR (CDCl$_3$, in ppm): δ 4.6 (s, m, 2H), 3.8 (m, s, 4H), 3.1 (s, s, 7H), 2.1–1.2 (complex, 29H).

EXAMPLE 12

This example discloses the synthesis of Uret7.

1) Synthesis of Hexylene-1,6-diisocyanate Bis-(cyclohex-3-enylmethyl) Carbamate

Following the same procedure as for phenylene-1,4-diisocyanate bis-(cyclohex-3-enylmethyl) dicarbamate except that the acetone solution of phenylene-1,4-diisocyanate was replaced by hexylene-1,6-diisocyanate, hexylene-1,6-diisocyanate bis-(cyclohex-3-enylmethyl) dicarbamate, in the form of a semi-solid, was obtained with 87% yield, and was identified by IR and NMR. IR (neat, in cm$^{-1}$): 3328, 2925, 2840, 1701, 1542, 1355, 1024, 780, 653. $^1$H NMR (CDCl$_3$, in ppm): δ 5.6 (s, s, 4H), 4.7–4.4 (d, w, 2H), 3.9 (d, s, 4H), 2.9 (d, m, 2H), 2.1–0.8 (complex, 24H). Its purity was verified by TLC.

2) Synthesis of Hexylene-1,6-diisocyanate Bis-(3,4-epoxycyclohexylmethyl) Dicarbamate (Uret7)

A Semi-solid Uret7 was obtained with 88% yield by following the same procedure as for Uret1. Its structure was identified by IR and NMR. IR (neat, in cm$^{-1}$): 3347, 2918, 1704, 1532, 1309, 1247, 1146, 1041, 792. $^1$H NMR (CDCl$_3$, in ppm): δ 4.7–4.4 (d, w, 2H), 3.8 (d, s, 4H), 3.1 (d, s, 4H), 2.9 (d, m, 2H), 2.1–0.8 (complex, 24H). The synthesis scheme for Uret4 through Uret7 is diagrammed below:

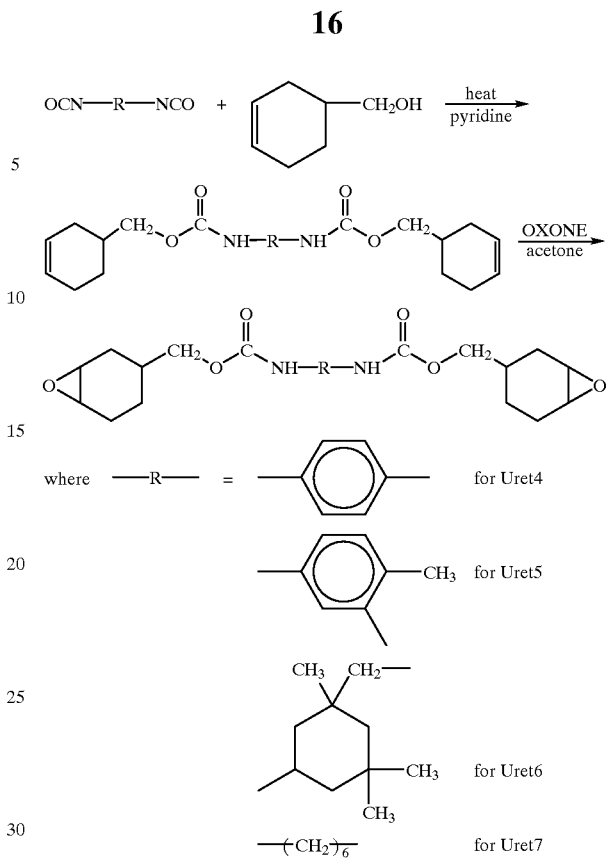

EXAMPLE 13

This example discloses Epoxide Equivalent Weights (EEWs) of Uret1 through Uret7.

The Epoxide Equivalent Weights (EEWs) of these diepoxides were measured according to ASTM titration procedure D1652-90. Table 2 shows their theoretical and measured FEW values. It can be seen that the measured values are in good agreement with the theoretical values.

TABLE 2

EEWs of Uret1 through Uret7

| Sample | EEW (g/mol.) | |
| --- | --- | --- |
| | Theoretical | Measured |
| Uret1 | 133.5 | 141 |
| Uret2 | 147.5 | 164 |
| Uret3 | 147.5 | 186 |
| Uret4 | 208 | 222 |
| Uret5 | 215 | 284 |
| Uret6 | 212 | 232 |
| Uret7 | 239 | 268 |

EXAMPLE 14

This example discloses structure of other chemicals used in the study.

Table 3 lists the chemical structures of a commercial epoxy resin, hardener and catalyst used in the experiments. The commercial epoxy resin, 3,4-epoxy cyclohexyl methyl-3,4-epoxy cyclohexyl carboxylate, was provided by Union Carbide under the Trade Name ERL4221 and used as received. Its Epoxide Equivalent Weight (EEW) is 133 g/mol. The hardener, hexahydro-4-methylphthalic anhydride (HHMPA), was purchased from Aldrich Chemical Company, Inc. and used as received. The catalyst, imidazole, was also purchased from Aldrich Chemical Company, Inc. and used as received.

One of ordinary skill in the art will recognize that a number of other compounds may be suitable for use with the cycloaliphatic epoxies of the present invention. For example, and not limitation, the organic hardener may also comprise any organic carboxylic acid anhydride hardener and in particular: hexahydrophthalic anhydride, methyl hexahydrophthalic anhydride, methyl-5-norbornene-2,3-dicarboxylic anhydride, tetrahydrophthalic anhydride, methyl tetrahydrophthalic anhydride, and nadic methyl anhydride. Other curing accelerators which may be suitable for use in accordance with the present invention include: triphenylphosphine, 2-ethyl-4-methyl imidazole, 1-(2-cyanoethyl)-2-ethyl-4-methylimidazole, imidazole, 1-methylimidazole, 1-benylimidazole, 1,2-dimethylimidazole, 1-benzyl-2-methylimidazole, 4-methyl-2-phenylimidazole, benzyldimethylamine, triethylamine, pyridine, dimethylaminopyridine, 1,4-diazabicyclo[2.2.2.]octane, 1,8-diazabicyclo[5.4.0]undec-7-ene, and 1,5-diazabicyclo[4.3.0]non-5-ene. Finally, the filler may selected from silica fillers with a variety of different particle sizes and particle size distributions.

The compositions of the present invention may be made suitable for use in no-flow chip mounting applications by the inclusion of a fluxing agent in the adhesive composition. The fluxing agent serves to remove oxidation from the solder bump and/or circuit pad and prevents reoxidation thereon, thereby facilitating the formation of electrical contacts during the chip mounting procedure. Fluxing agents suitable for use in the present invention include, for example and not limitation: glycerol, glycerin, formic acid, acetic acid, tartaric acid, malic acid and citric acid. One of ordinary skill in the art will recognize that a variety of other fluxing agents may also be useful in accordance with the spirit of the present invention, such as organic acids or low vapor pressure alcohols.

TABLE 3

Chemical Ingredients Used for Reworkable Epoxy Sample Preparation

| Name of chemicals | Structure of Chemicals |
|---|---|
| ERL4221 | |
| HHMPA | |
| Imidazole | |

EXAMPLE 15

An electro-magnetic stirrer was used to mix the epoxy resin, hardener, and catalyst. The four synthesized diepoxides were mixed with HHMPA, respectively, in a mole ratio 1:0.8 and 1% in weight of catalyst imidazole, and were called Epocarb1 through Epocarb4. ERL4221 was also mixed with HHMPA and imidazole in the same ratio and was called Epo0 (see Table 4). The mixture was stirred until a homogeneous phase was formed.

TABLE 4

Composition of Epo0 and Epocarb1 Through Epocarb4

| Sample | Epoxide/Anhydride (1/0.8 mol) | Catalyst (1 wt %) |
|---|---|---|
| Epo0 | ERL4221/HHMPA | Imidazole |
| Epocarb1 | Carb1/HHMPA | Imidazole |
| Epocarb2 | Carb2/HHMPA | Imidazole |
| Epocarb3 | Carb3/HHMPA | Imidazole |
| Epocarb4 | Carb4/HHMPA | Imidazole |

EXAMPLE 16

It was found that carbonate linkage inside the epoxide structure did not react with epoxy composition and was inert to epoxy curing due to the fact that carbonate linkage was a fairly chemically stable group. FIG. 1 shows the curing profiles of four formulations based on these four epoxides as compared to Epo0. It can be seen that they all cured similarly compared to Epo0. Endothermic peaks for Epocarb3 and Epocarb4 around 200° C. were caused by decomposition.

EXAMPLE 17

Figure 2:
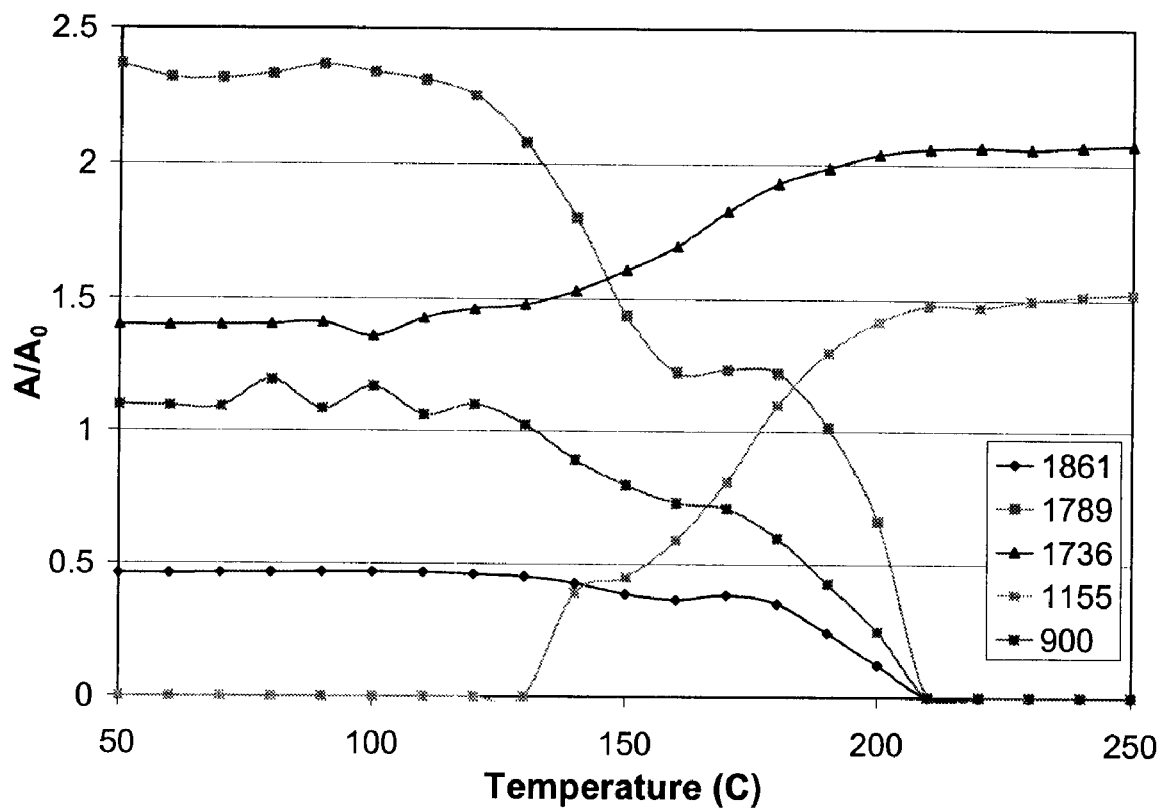
FIG. 2 is a graph illustrating the normalized FT-IR absorbance of Epocarb2 from room temperature to 250° C. at a heating rate of 10° C./min.

Time-resolved FT-IR proved to be a useful tool to monitor the curing and degradation of epoxy system. IR spectra of Epocarb4 were collected at different temperatures at a heating rate of 10° C./min and analyzed. The curing process was easily monitored by a decrease in absorbance at 1864 and 1789 cm$^{-1}$ (HHMPA anhydride C=O stretching) and at 901 cm$^{-1}$ (epoxide C—O—C ring deformation). Furthermore, the increase of the absorbance at 1155 cm$^{-1}$ (ester C—O stretching) and 1736 cm$^{-1}$ (ester C=O stretching) is the clear sign of ester formation during the epoxy-anhydride curing. The absorbance at 1266 cm$^{-1}$ (carbonate C—O stretching) was used as an internal standard to normalize the baseline and film thickness change of the sample during reaction. FIG. 2 shows the normalized FT-IR absorbance of Epocarb2 from room temperature to 250° C.

EXAMPLE 18

Figure 3:
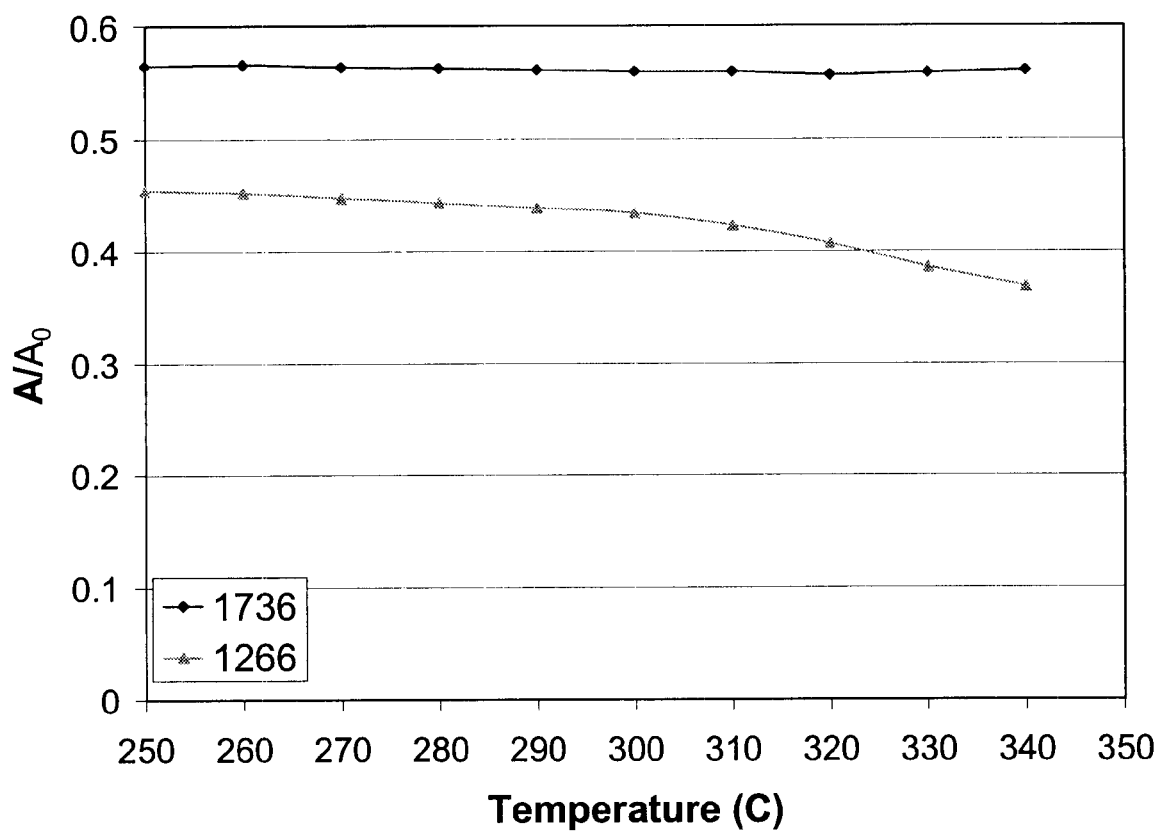
FIG. 3 is a graph illustrating the normalized FT-IR absorbance of Epocarb2 from 250° C. to 350° C. at a heating rate of 10° C./min.

Degradation of Epocarb2 was studied by analyzing its IR spectra from 250° C. to 350° C. While the absorbance at 1736 and 1155 cm$^{-1}$ decreased slightly which was probably caused by the film thickness change, the absorbance at 1266 cm$^{-1}$ decreased much faster. FIG. 3 shows the normalized FT-IR absorbance (by 1155 cm$^{-1}$) of Epocarb2 from 250° C. to 350° C. The decrease of 1266 cm$^{-1}$ was caused by the thermal cleavage of carbonate linkage, which is the mechanism for Epocarb2 degradation. Other samples were also studied by time-resolved FT-IR and similar results were obtained.

EXAMPLE 19

Figure 4:
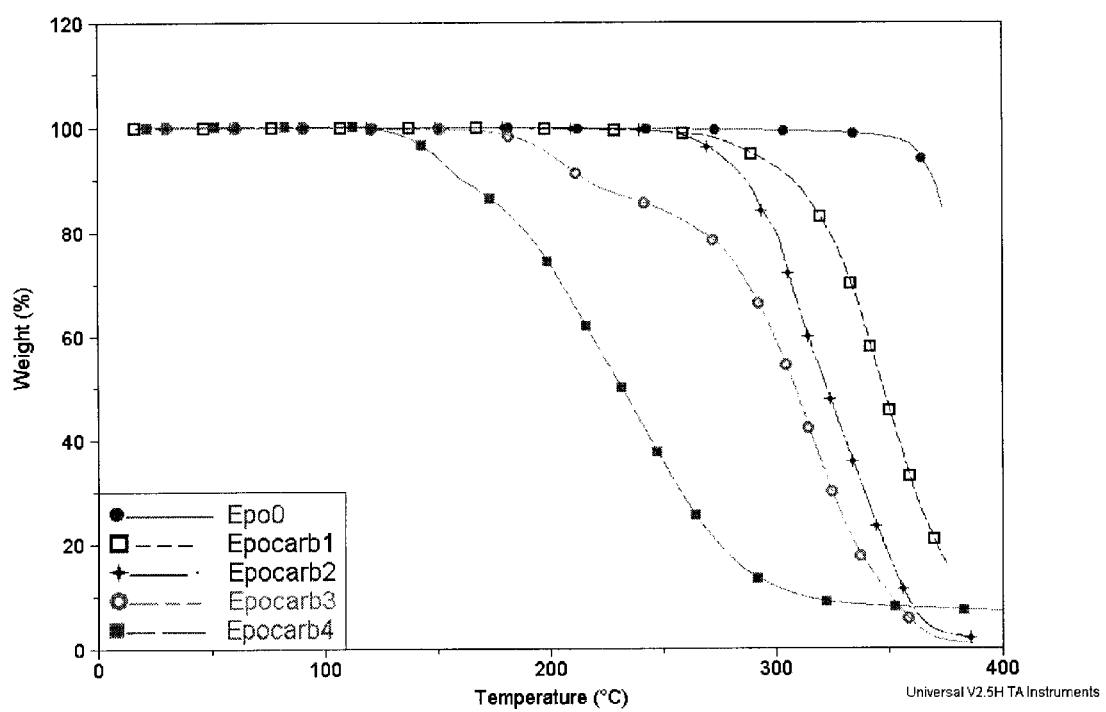
FIG. 4 is a graph illustrating TGA curves for Epo0 and Epocarb1 through Epocarb4.

FIG. 4 shows the TGA curves of the cured samples at a heating rate of 10° C./min. It is clear that all these samples based on carbonate-containing epoxides degraded at lower temperature than that based on ERL4221. In addition, it can be drawn from the figure that thermal stability of these epoxides in very general terms goes in the following order: tertiary carbonate<secondary carbonate<primary carbonate.

EXAMPLE 20

Degradation kinetics of epoxy can be described by the following equation:

ln R=ln (dα/dt)=F+ln A—E/RT where R is reaction rate, α is conversion, t is time, F is a constant, A is the pre-exponential factor and E is activation energy. Degradation kinetics of Epo0, Epocarb1 and Epocarb2 was studied by using TGA at four different heating rates. At different degree of conversion and temperature, the degradation kinetics may be different and can be influenced by many factors including sample shape, volatility, local atmosphere and thermal transfer. So all samples were tested under the same TGA conditions. The activation energy of the thermal decomposition as calculated above (see Table 5) is the average activation energy at low conversion, α=0.01–0.10, which is due to the initial decomposition of the weak linkages. Epo0 (primary ester linkage) had higher activation energy than Epocarb1 (primary carbonate linkage), and Epocarb1 had higher activation energy than Epocarb2 (secondary carbonate linkage). It can be seen that these calculated activation energy results are in good accordance with the onset decomposition temperatures of these three materials.

TABLE 5

Thermal Decomposition Activation Energies of Epo0, Epocarb1 and Epocarb2 Calculated from TGA Kinetics

| Sample | Activation Energy $E_a$ (kJ/mol) |
| --- | --- |
| Epo0 | 152.7 |
| Epocarb1 | 124.8 |
| Epocarb2 | 112.3 |

EXAMPLE 21

Figure 5:
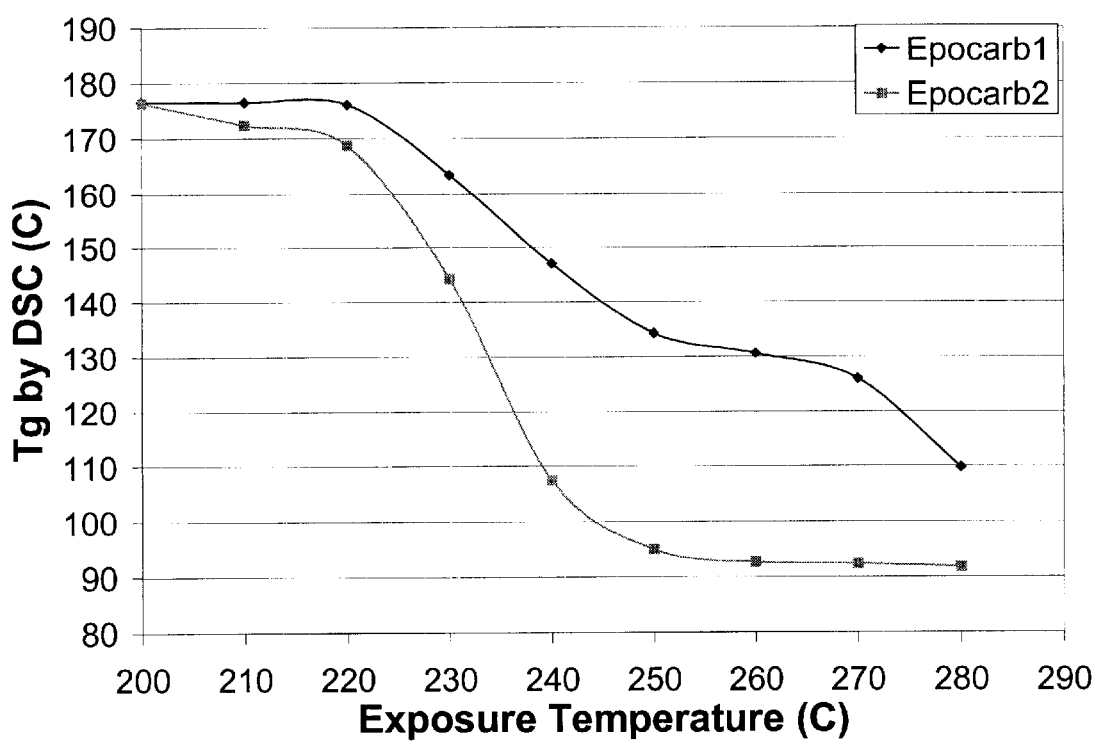
FIG. 5 is a graph illustrating a Tg-exposure temperature plot for Epocarb1 and Epocarb2.

TGA results show that Epocarb1 and Epocarb2 started weight loss around 250° C., which is much higher than the targeted rework temperature, 220° C. However, TGA is not a very good tool to determine network break-down temperature because it can only measure weight loss vs. temperature, but the network may have already partially broken down even though the products are not volatile enough to produce any detectable mass change. Therefore, it was decided to use Tg change of the epoxy network to represent the network break-down. First, ten specimens of each epoxy formulation were prepared by curing at 175° C. for 30 minutes. Among these specimens, nine were then exposed to different temperatures by staying in a preheated oven for 5 minutes. The temperature ranged from 200 to 280° C. for every 10° C. increment. Then the Tgs of these nine high temperature treated specimens and the non-treated specimen were determined by DSC. FIG. 5 shows the Tg vs. exposure temperature curve for Epocarb1 and Epocarb2. It shows that both formulations had network-break down temperature around 220° C., which is suitable for use as a reworkable adhesive. It also shows that Epocarb2 had network break-down much faster than Epocarb1, which can be explained by the less thermal stability of secondary carbonate linkage than primary carbonate linkage.

EXAMPLE 22

Various properties of Epocarb1 and Epocarb2 were measured and compared to those of Epo0. Table 6 lists the Tg, CTE, Storage Modulus, and room temperature viscosity of Epocarb1 and Epocarb2 as compared to Epo0. It is clear that both Epocarb1 and Epocarb2 were comparable to Epo0 in any of these categories.

TABLE 6

Properties of Epo0, Epocarb1, and Epocarb2

| Sample | Epo0 | Epocarb1 | Epocarb2 |
| --- | --- | --- | --- |
| Tg (° C.) | 175 | 176 | 176 |
| CTE (ppm/° C., 50–100° C.) | 75 | 76 | 85 |
| Storage Modulus (GPa, at 25° C.) | 2.6 | 2.8 | 2.5 |
| Viscosity (Pa · S, At 25° C.) | 0.24 | 0.30 | 0.34 |

EXAMPLE 23

Figure 6:
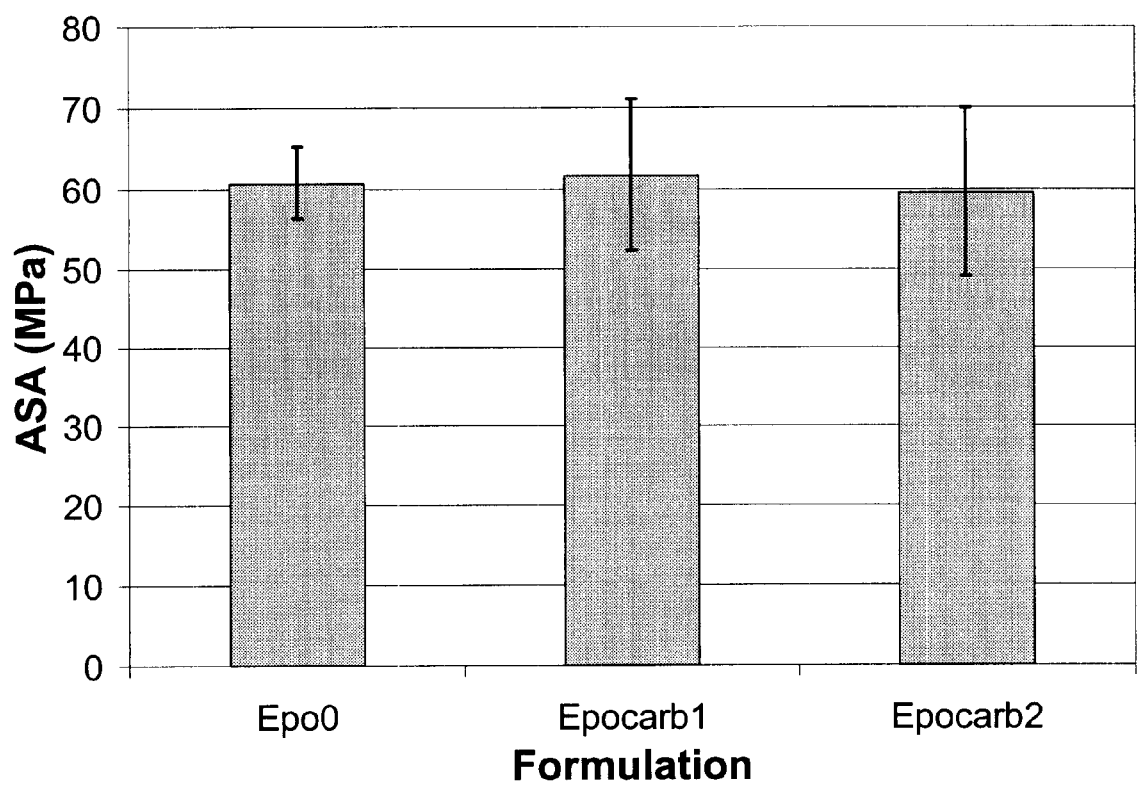
FIG. 6 is a graph illustrating the relative adhesion of Epo0 and Epocarb1 through Epocarb4.

The adhesion of Epocarb1 and Epocarb2 was also studied. FIG. 6 shows the adhesion data of Epocarb1, Epocarb2 and Epo0, which shows both Epocarb1 and Epocarb2 had comparable adhesion compared to Epo0.

EXAMPLE 24

Figure 7:
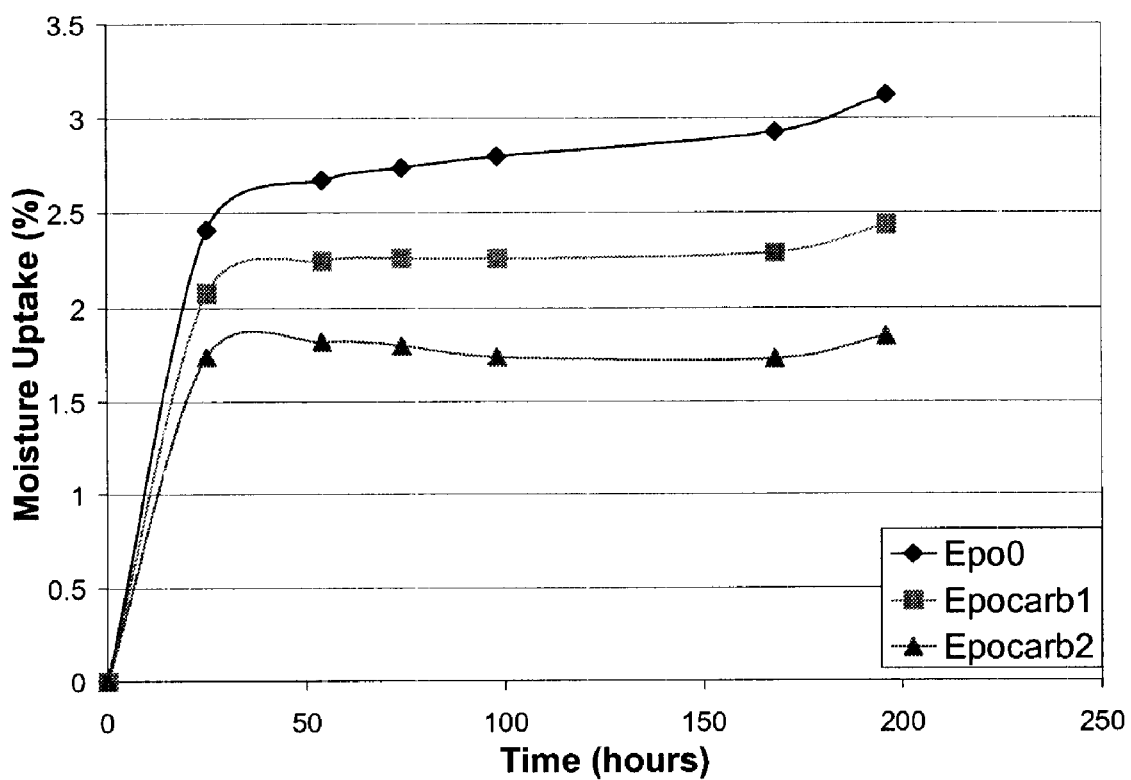
FIG. 7 is a graph illustrating Moisture Uptake Data of Epo0, Epocarb1 and Epocarb2.

Moisture uptake of Epocarb1 and Epocarb2 was measured and compared to that of Epo0. FIG. 7 shows the results from moisture uptake measurements. The moisture uptake of Epocarb1 and Epocarb2 was lower than Epo0, which can be explained by the less hydrophilicity of carbonate group than ester group. The fact that Epocarb2 picked up less moisture than Epocarb1 could be explained by the less hydrophilicity of Carb2 than Carb1 with the additional methyl group.

EXAMPLE 25

This example discloses the chemicals and formulations used to study Uret1 through Uret7.

ERL4221 was used as the epoxy resin while HHMPA was used as the hardener. The catalyst, 1-cyanoethyl-2-ethyl-4-methylimidazole (EMZCN), was provided by Shikoku company and used as received.

An electro-magnetic stirrer was used to mix the epoxy resin, hardener, and catalyst. The seven synthesized diepoxides were mixed with HHMPA, respectively, in a mole ratio 1:0.8 and 4 wt % of catalyst EMZCN, and were called Epouret1 through Epouret7. ERL4221 was also mixed with HHMPA and EMZCN in the same ratio and was called Epoxy0 (see Table 7). The mixture was stirred until a homogeneous phase was formed.

TABLE 7

Composition of Epoxy0 and Epouret1 Through Epouret7

| Sample | Epoxide/Anhydride (1/0.8 mol) | Catalyst (4 wt %) |
| --- | --- | --- |
| Epoxy0 | ERL4221/HHMPA | EMZCN |
| Epouret1 | Uret1/HHMPA | EMZCN |
| Epouret2 | Uret2/HHMPA | EMZCN |
| Epouret3 | Uret3/HHMPA | EMZCN |
| Epouret4 | Uret4/HHMPA | EMZCN |
| Epouret5 | Uret5/HHMPA | EMZCN |
| Epouret6 | Uret6/HHMPA | EMZCN |
| Epouret7 | Uret7/HHMPA | EMZCN |

EXAMPLE 26

Figure 8:
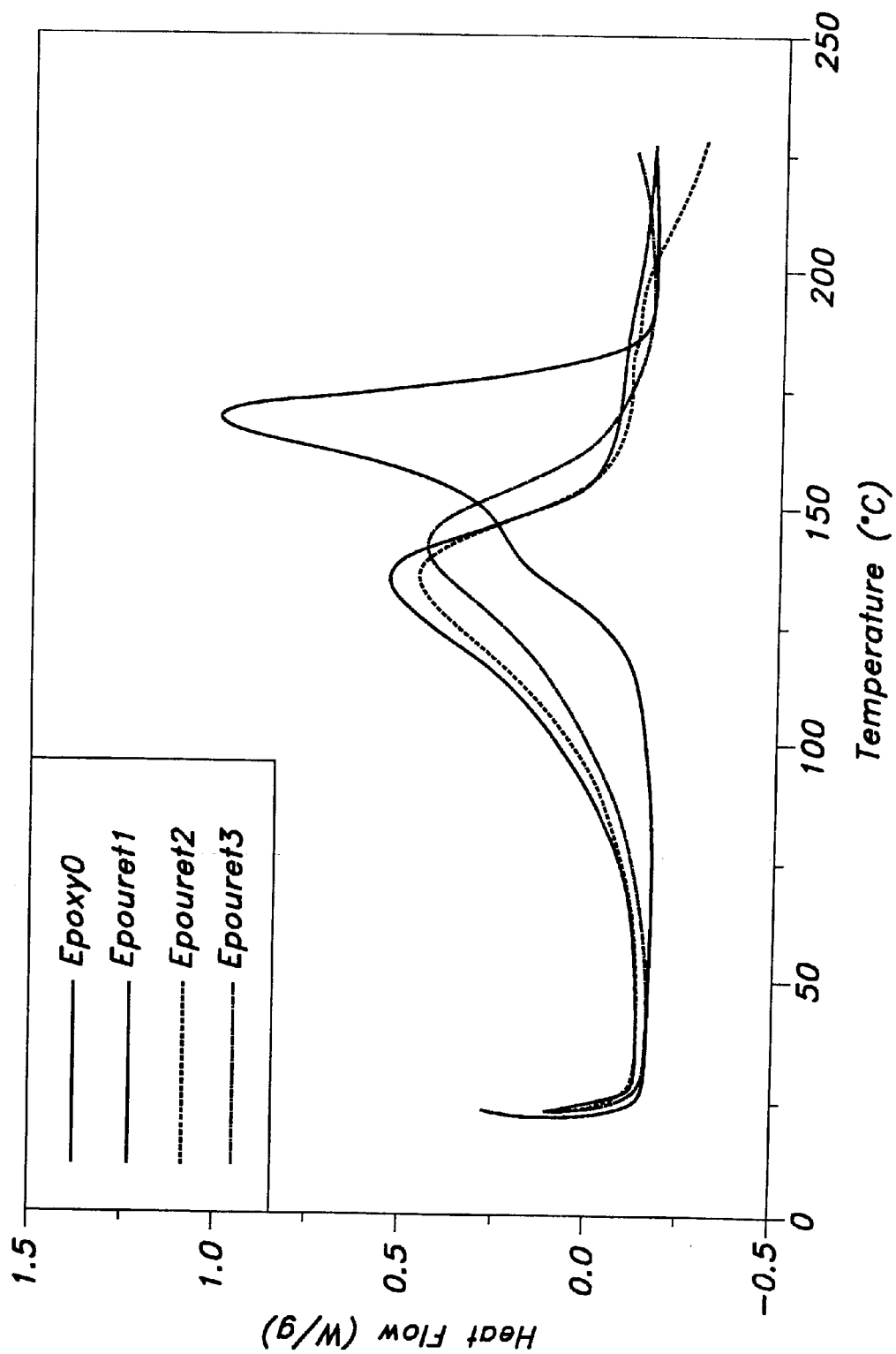
FIG. 8 is a graph illustrating DSC cooling curves of Epoxy0 and Epouret1 through Epouret3.
Figure 9:
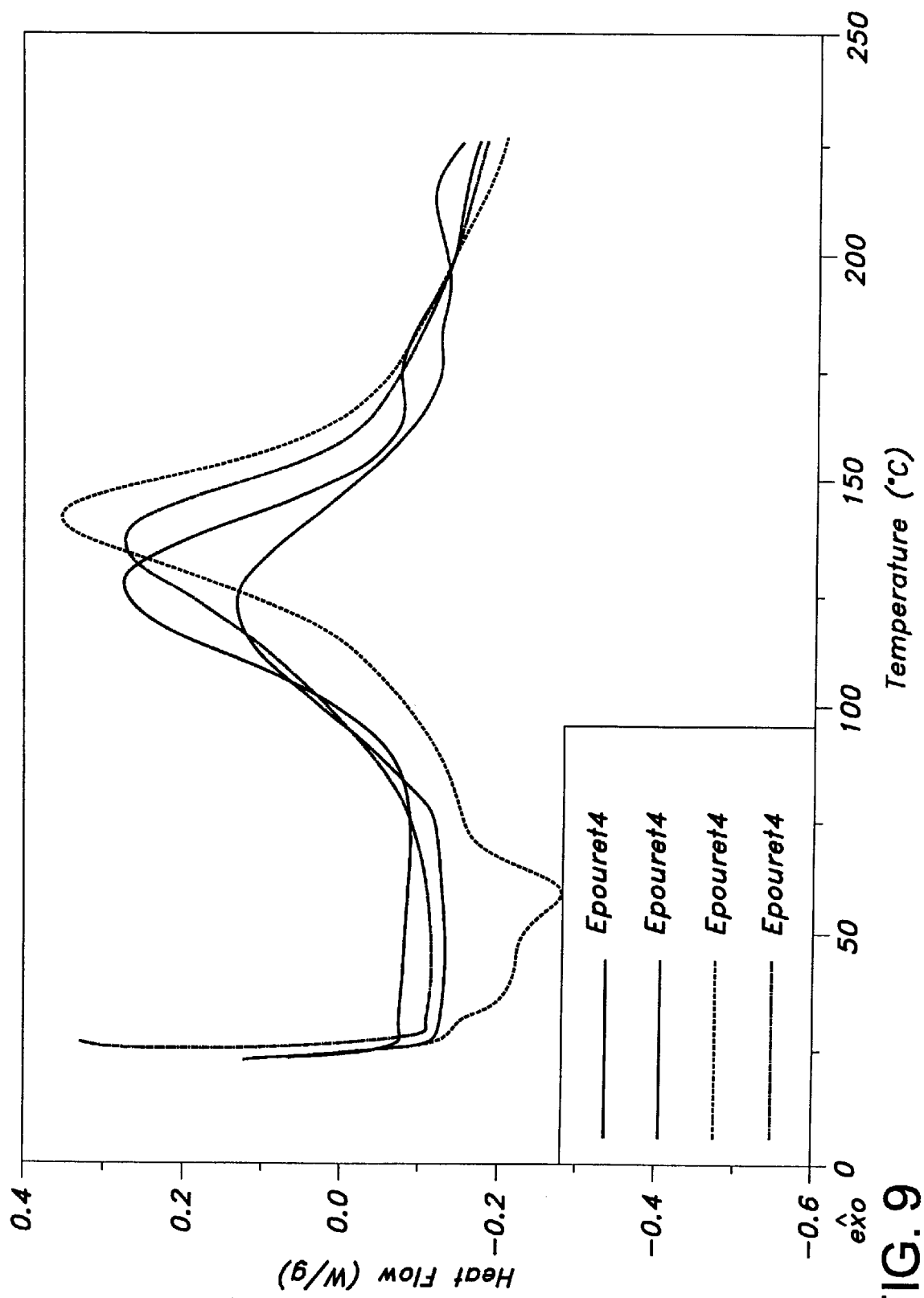
FIG. 9 is a graph illustrating DSC cooling curves of Epouret4 through Epouret7.

FIG. 8 shows the curing profiles of formulations Epoxy0 through Epouret3. FIG. 9 shows the curing profiles of Epouret4 through Epouret7. It is clear that Epoxy0 cured at a higher temperature region than the other formulations. This indicated that there might be some interactions between the carbamate linkage and epoxy curing, causing the peak of epoxy curing to shift to a lower temperature region.

EXAMPLE 27

Figure 10:
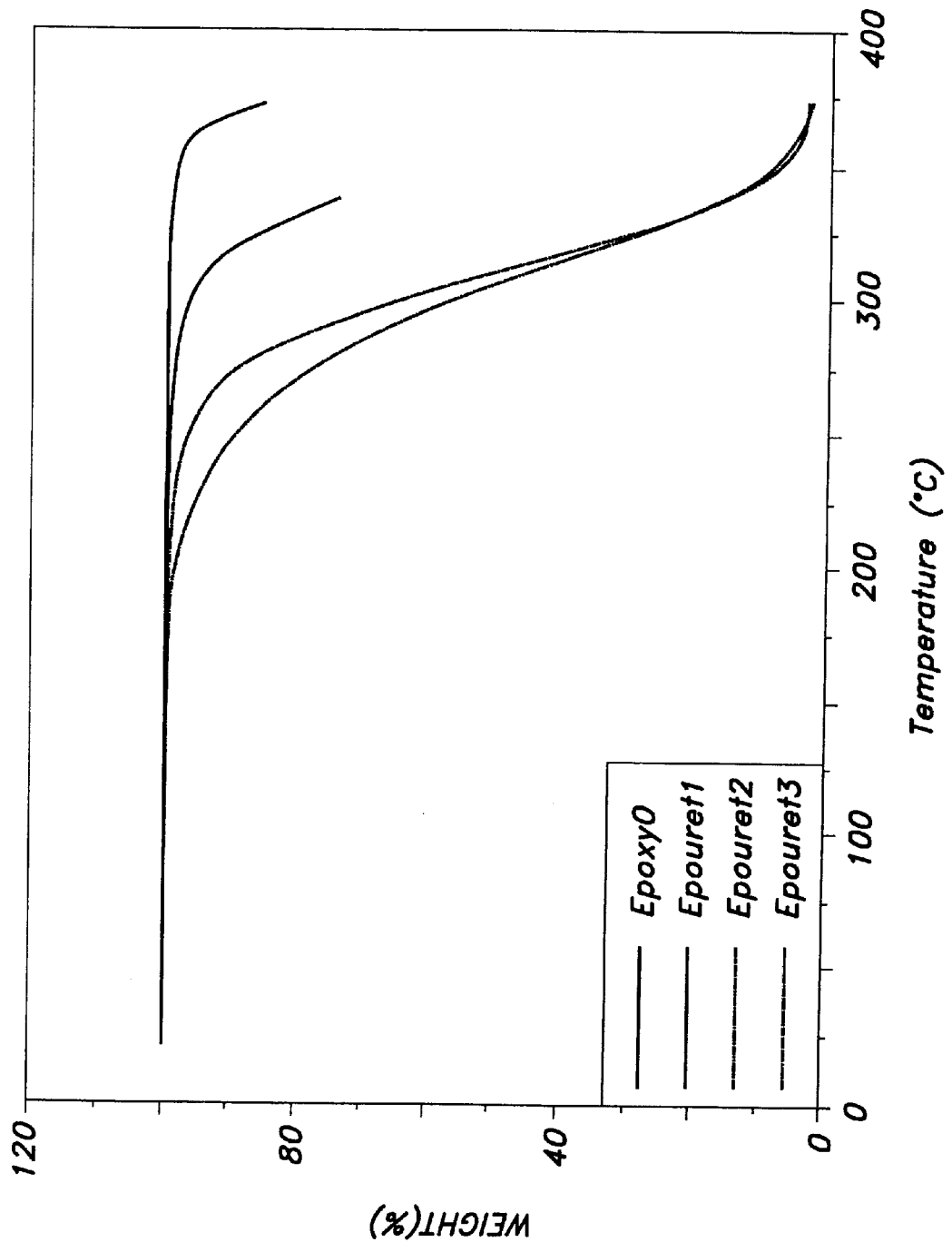
FIG. 10 is a graph illustrating TGA curves of Epoxy0 and Epouret1 through Epouret3.

FIG. 10 shows the TGA curves of cured samples Epoxy0 through Epouret3. It clearly shows that the sample from ERL4221 was quite thermally stable. It did not start losing weight until after 350° C. For the three cured samples from liquid formulations, Epouret1 through Epouret3, decomposition started at much lower temperatures. By comparing the curve of Epouret1, which showed its onset decomposition temperature around 280° C., to the curve of Epouret2, which showed its onset decomposition temperature around 220° C., it is clear that the carbamate group from a tertiary alcohol degraded at a much lower temperature than the one from a primary alcohol.

Figure 11:
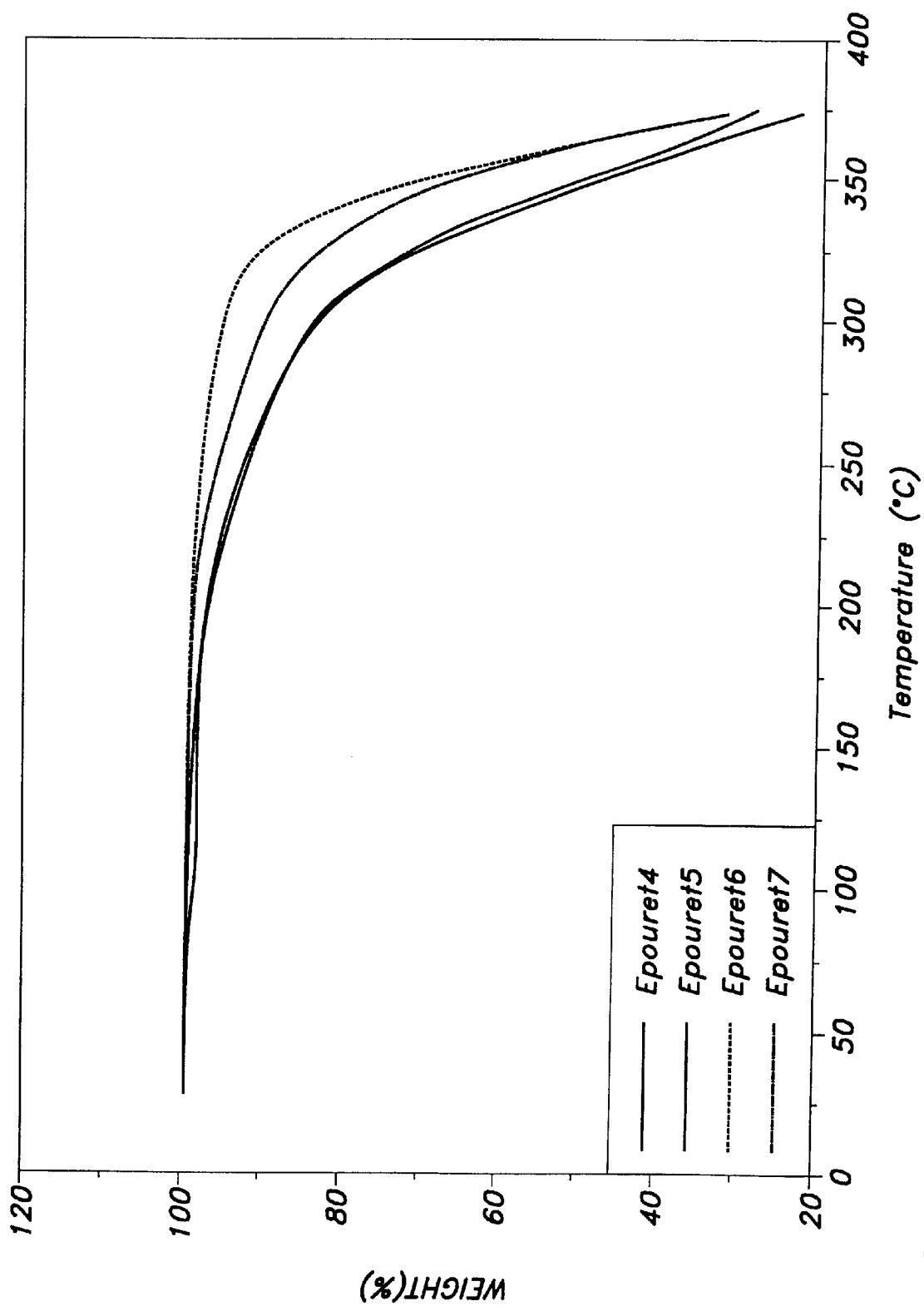
FIG. 11 is a graph illustrating TGA curves of Epouret4 through Epouret7.

FIG. 11 shows the TGA curves of the formulations from the four solid diepoxies, Epouret4 through Epouret7. The formulations using solid diepoxies started to decompose at temperatures below 300° C. Moreover, the two formulations from Uret6 and Uret7—Epouret6 and Epouret7—had higher onset decomposition temperatures than Epouret4 and Epouret5.

EXAMPLE 28

This example discloses the composition of a thermally reworkable underfill formulation based on Carb1 as shown in Table 8. This formulation is named GT-1".

TABLE 8

| | Composition of GT-1" | | | | |
|---|---|---|---|---|---|
| Sample | Epoxide/Anhydride (1/0.8 mol) | Imidazole (1 wt %) | Filler Loading | Silane (1 wt %) | Tougher (10 mole %) |
| GT-1" | Carb1/HHMPA | Y | 50% | Y | Y |

EXAMPLE 29

This example discloses a developed rework process.

Chip Removal

Figure 12:
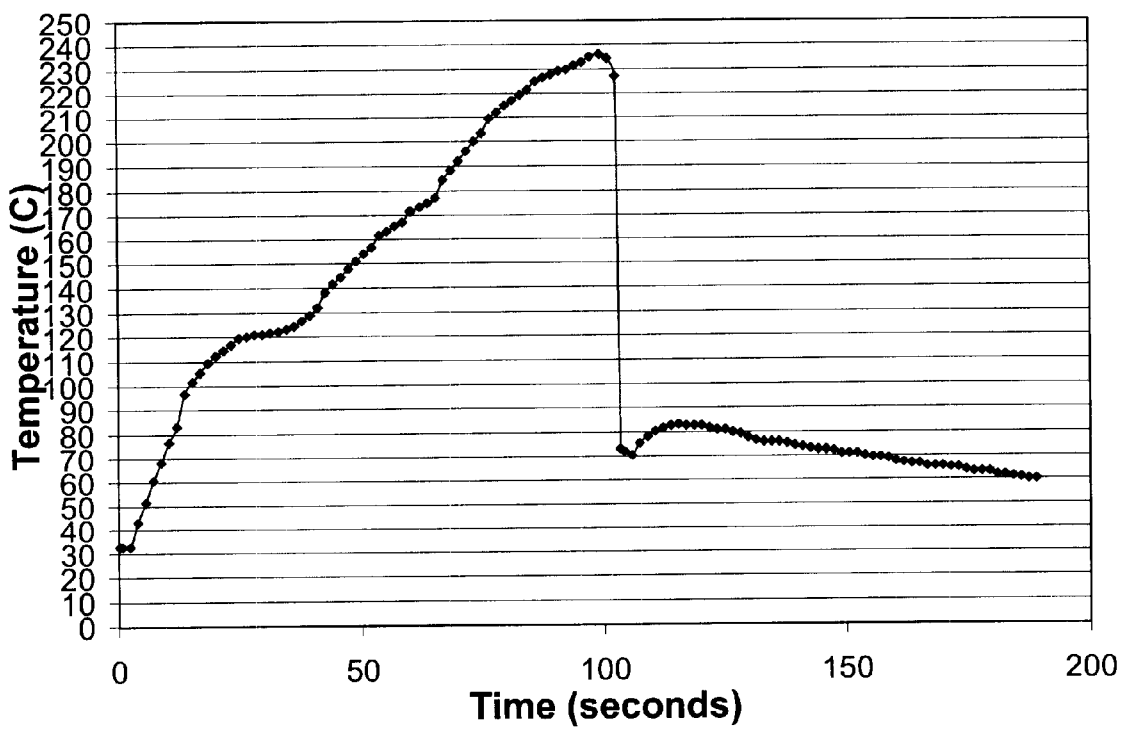
FIG. 12 is a temperature profile of a thermocouple on the board during chip removal testing.

Chip removal test was conducted on the rework station using assembled and underfilled flip chip test boards. Temperature profile of the board site during chip removal was obtained by monitoring the actual temperature inside the board during chip removal through a buried thermal couple. Through adjusting various machine parameters and checking the subsequent temperature profiles of the board site, a chip removal profile allowing the board site to reach desired rework temperature without damaging the board was obtained. This chip removal profile was found to loosen the reworkable underfill at peak temperature. The major steps of the profile is listed as follows:

1. Preheat
   Top and bottom heater was set at 200° C. The board was heated until 25 seconds had passed since the preset temperature was reached.
2. Activate
   Top and bottom heater was set at 270° C. The board was heated until 20 seconds had passed since the preset temperature was reached.
3. Adjust Head Position
4. Reflow
   Top heater was set at 380° C. while the bottom heater was set to 400° C. The board was heated until 30 seconds had passed since the preset temperature was reached.
5. Remove Part FIG. 12 shows the temperature profile of the board using the established chip removal profile.

Figure 13:
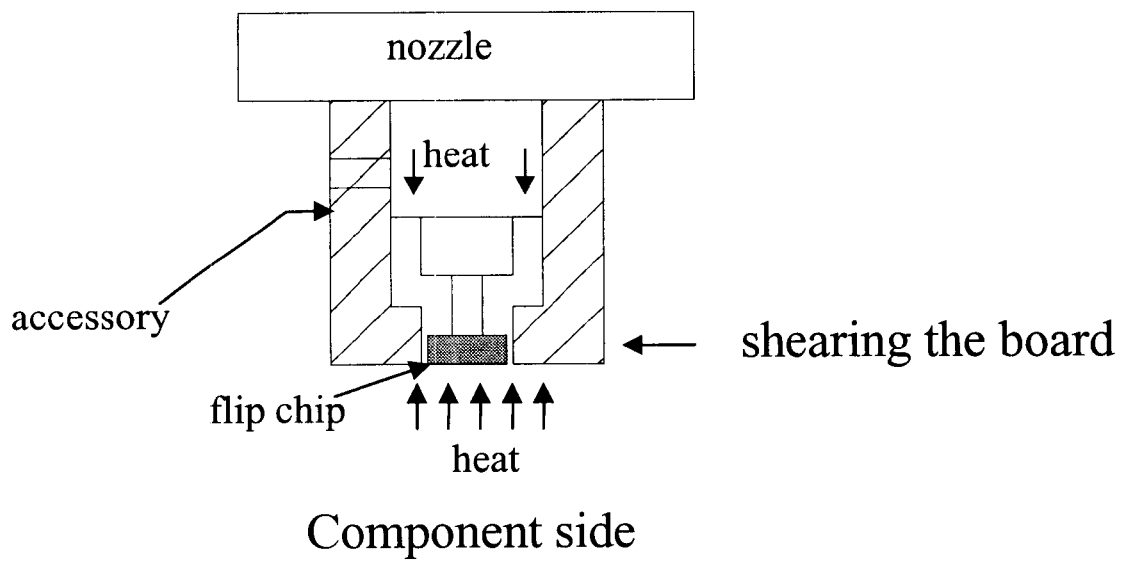
FIG. 13 is a schematic of an accessory designed for flip-chip rework.

By using this rework profile, non-underfilled chips were found to be easily removed by the vacuum force applied through the nozzle. However, the nozzle could not remove the underfilled chips from the board because the vacuum force was not strong enough. An accessory was then designed, manufactured, and mounted onto the small nozzle for flip chip rework. The schematic of this design is shown in FIG. 13. The idea was to have the accessory holding the chip during the rework. This would allow shear or twisting force to be applied to the chip.

This accessory was put to test. After the nozzle touched the chip, the frame that held the board was slowly moved in both X and Y directions in order to apply a shear force on the chip. This was found to not only apply the shear force to the chip, but also help remove part of the underfill fillet, which helped the subsequent site-cleaning step as the underfill fillet was the most difficult part to remove. After that, the chip was lifted up by the nozzle and removed from the board.

Site-Cleaning

Figure 14:
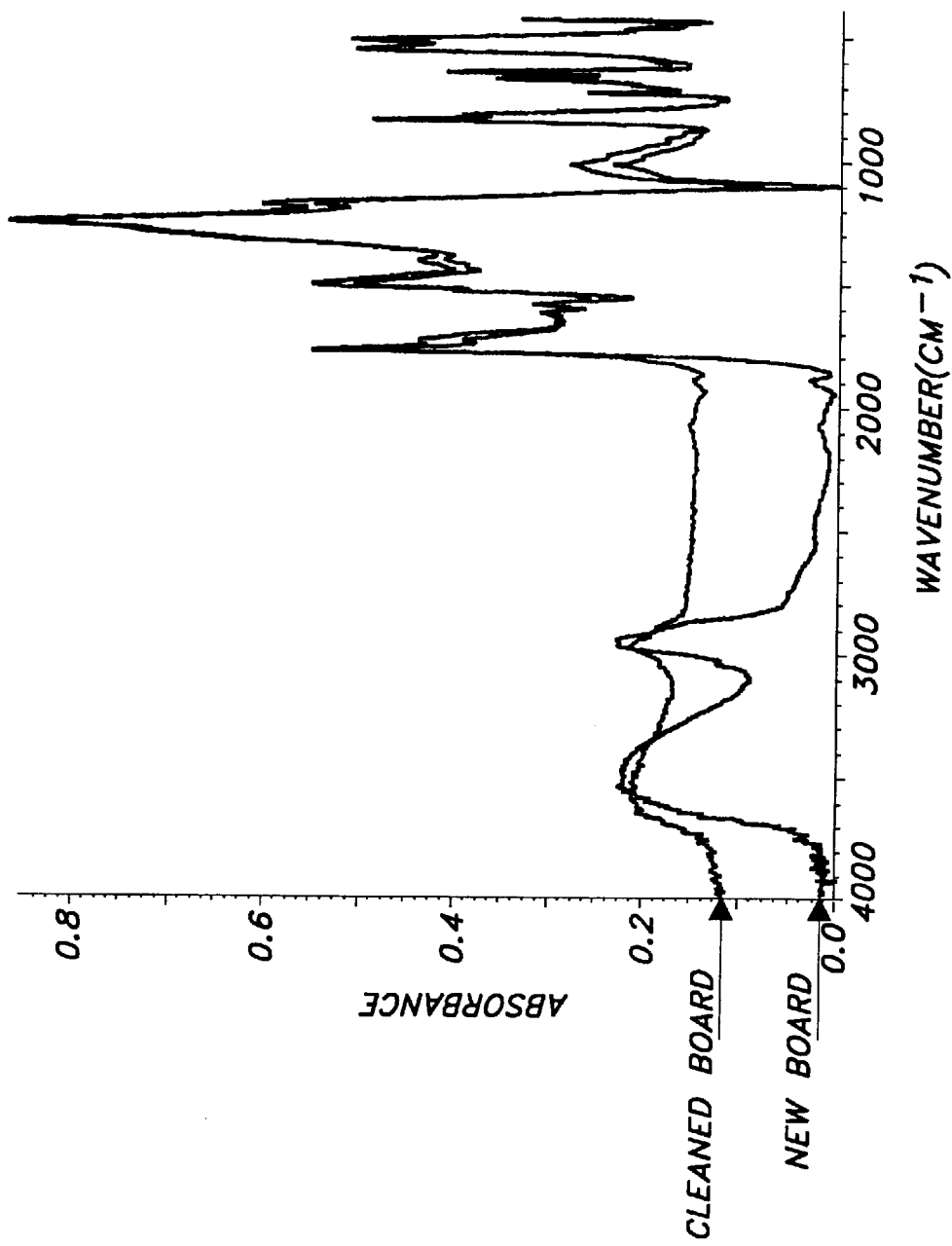
FIG. 14 illustrates FT-IR spectra of a clean board and a board after cleaning.

After chip removal, the underfill residue and solder residue had to be cleaned and the site prepared to accept a new chip. Different cleaning methods were tried and the combination of a gentle mechanical process with solvent cleaning worked best. The mechanical cleaning was done by using a horsehair brush which was attached to a Dremel tool to slowly and carefully sweep away the underfill residue. The debris generated during the mechanical cleaning was then removed by isopropyl alcohol (IPA). This cleaning method was found to clean the underfill residue and the solder residue simultaneously with minimum damage to the solder mask and bump pads on the FR-4 board. FIG. 14 shows the comparison of the IR spectrum of a board after clean vs. a clean board. Both spectra matched well, indicating that the board was clean after the cleaning step.

Chip Replacement

New chips were assembled on the reworked sites following the same procedure for test vehicle assembly. Inspecting replaced chips using continuity test and x-ray machine found that good solder interconnects were formed. High yield chip replacement was achieved on the replaced chips, which indicated that the cleaning process maintained the integrity of the bond pads.

EXAMPLE 30

This example discloses the rework test results of GT-1". Flip chips underfilled with GT-1" could be reworked using the above rework process. Underfill and solder residue were removed during the cleaning process. The bond pads at the rework site kept their integrity. New chips were placed on the reworked sites and good electrical continuity was achieved.

EXAMPLE 31

This example discloses a reliability test for GT-1".
Reliability of underfilled flip chips was measured by subjecting the boards to liquid-to-liquid thermal shock (LLTS) test using an ESPEC Thermal Shock Chamber. The test condition was 10-minute cycle from −55 to 125° C., with 5 minutes cold and 5 minutes hot.

EXAMPLE 32

This example discloses reliability test results for GT-1". Average number of cycles a flip chip underfilled with GT-1" could withstand is 1500 cycles, which is comparable to a high performance commercial non-reworkable underfill.

What is claimed is:

1. A thermally reworkable epoxy composition, said composition comprising the cured product of:
   a cycloaliphatic epoxy, wherein said cycloaliphatic epoxide contains a carbamate group;
   an organic hardener;
   a curing accelerator; and
   a fluxing agent,
   wherein said composition is thermally degradable between approximately 200° C. and 250° C.

2. The epoxy composition of claim 1, wherein said cycloaliphatic epoxide is selected from the group consisting of: 3,4-epoxycyclohexyl-1-isocyanate 3,4-epoxycyclohexylmethyl carbamate; 3,4-epoxycyclohexyl-1-isocyanate 2-(3,4-epoxycyclohexyl)-2-propyl carbamate; 3,4-epoxycyclohexylmethyl 2-(1,2-epoxycyclohexyl)ethyl carbamate; phenylene-1,4-diisocyanate Bis-(3,4-epoxycyclohexylmethyl) dicarbamate; tolylene-2,4-diisocyanate Bis-(3,4-epoxycyclohexylmethyl) dicarbamate; isophorone diisocyanate Bis-(3,4-epoxycyclohexylmethyl) dicarbamate; and hexylene-1,6-diisocyanate Bis-(3,4-epoxycyclohexylmethyl) dicarbamate.

3. The epoxy composition of claim 1, wherein said organic hardener is selected from the group consisting of: hexahydrophthalic anhydride, methyl hexahydrophthalic anhydride, methyl-5-norbornene-2,3-dicarboxylic anhydride, tetrahydrophthalic anhydride, methyl tetrahydrophthalic anhydride, and nadic methyl anhydride;
   said curing accelerator is selected from the group consisting of: triphenylphosphine, 2-ethyl-4-methyl imidazole, 1-(2-cyanoethyl)-2-ethyl-4-methylimidazole, imidazole, 1-methylimidazole, 1-benylimidazole, 1,2-dimethylimidazole, 1-benzyl-2-methylimidazole, 4-methyl-2-phenylimidazole, benzyldimethylamine, triethylamine, pyridine, dimethylaminopyridine, 1,4-diazabicyclo[2,2,2]octane, 1,8-diazabicyclo[5,4,0]undec-7-ene, and 1,5-diazabicyclo[4,3,0]non-5-ene; and
   said fluxing agent is selected from the group consisting of: glycerol, glycerin, formic acid, acetic acid, tartaric acid, malic acid, citric acid and mixtures thereof.

4. The epoxy composition of claim 1, wherein said organic hardener exists in a ratio of 20.0 to 80.0 parts by weight to 50 parts of said cycloaliphatic epoxide;
   said curing accelerator exists in a ratio of 0.05 to 1.0 parts by weight to 50 parts of said cycloaliphatic epoxide; and
   said fluxing agent exists in a ratio of 1.0 to 10.0 parts by weight to 50 parts of said cycloaliphatic epoxide.

5. The epoxy composition of claim 1, further comprising a silica filler.

6. The epoxy composition of claim 1, wherein said composition is thermally degradable at a temperature of approximately 220° C.

7. A thermally reworkable epoxy composition, said composition comprising the cured product of:
   an organic hardener;
   a curing accelerator; and
   a cycloaliphatic epoxide having the structural formula $$A-\underset{R_2}{\overset{R_1}{C}}-O-\overset{O}{\underset{\|}{C}}-O-A^1$$

wherein $R_1$ and $R_2$ are independently selected from the group consisting of hydrogen, methyl, ethyl, propyl, isopropyl, butyl, sec-butyl, tert-butyl, isobutyl, and phenyl; and A is

[structure of substituted epoxycyclohexyl group with R substituents]

wherein each R is independently selected from the group consisting of hydrogen, methyl, ethyl, propyl, isopropyl, isobutyl, sec-butyl, tert-butyl, halogen, cyano, nitro, and phenyl; and $A^1$ is $$-\underset{R_4}{\overset{R_3}{C}}-R_5$$

wherein $R_3$, $R_4$, and $R_5$ are each independently selected from a group consisting of methyl, ethyl, propyl, isopropyl, butyl, sec-butyl, tert-butyl, isobutyl, and phenyl or $A^1$ is

[structure of substituted dioxolane-phenyl group with R substituents]

8. The compounds of claim 7 having the structural formula:

[structure showing dioxolane-phenyl linked through C(R_1)(R_2)-O-C(=O)-O- to substituted epoxycyclohexyl group]

9. the compound of claim 7 having the structural formula:

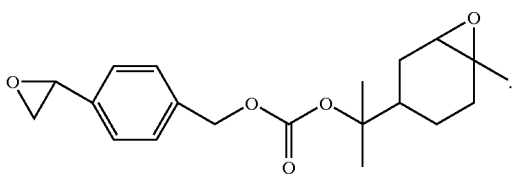

10. The compounds of claim 7 having the structural formula:

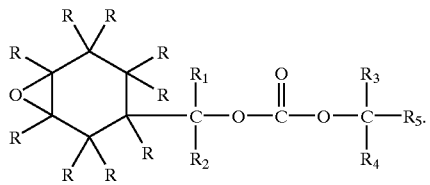

11. The compound of claim 7 having the structural formula:

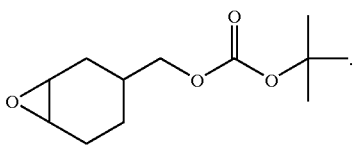

12. The epoxy composition of claim 7, further comprising a fluxing agent.

13. The epoxy composition of claim 12, wherein said organic hardener is selected from the group consisting of: hexahydrophthalic anhydride, methyl hexahydrophthalic anhydride, methyl-5-norbornene-2,3-dicarboxylic anhydride, tetrahydrophthalic anhydride, methyl tetrahydrophthalic anhydride, and nadic methyl anhydride;

said curing accelerator is selected from the group consisting of: triphenylphosphine, 2-ethyl-4-methyl imidazole, 1-(2-cyanoethyl)-2-ethyl-4-methylimidazole, imidazole, 1-methylimidazole, 1-benylimidazole, 1,2-dimethylimidazole, 1-benzyl-2-methylimidazole, 4-methyl-2-phenylimidazole, benzyldimethylamine, triethylamine, pyridine, dimethylaminopyridine, 1,4-diazabicyclo[2,2,2]octane, 1,8-diazabicyclo[5,4,0]undec-7-ene, and 1,5-diazabicyclo[4,3,0]non-5-ene; and said fluxing agent is selected from the group consisting of: glycerol, glycerin, formic acid, acetic acid, tartaric acid, malic acid, citric acid and mixtures thereof.

14. The epoxy composition of claim 12, wherein said organic hardener exists in a ratio of 20.0 to 80.0 parts by weight to 50 parts of said cycloaliphatic epoxide;

said curing accelerator exists in a ratio of 0.05 to 1.0 parts by weight to 50 parts of said cycloaliphatic epoxide; and said fluxing agent exists in a ratio of 1.0 to 10.0 parts by weight to 50 parts of said cycloaliphatic epoxide.

15. The epoxy composition of claim 7, further comprising a silica filler.

16. The epoxy composition of claim 7, wherein said composition is thermally degradable at a temperature between approximately 200° C. and 250° C.

17. The epoxy composition of claim 7, wherein said composition is thermally degradable at a temperature of approximately 220° C.

18. A method of protecting a device with a cured thermally reworkable epoxy composition, the method comprising the steps of:

reacting a thermally degradable cycloaliphatic epoxide, wherein said cycloaliphatic epoxide contains a carbamate group; an organic hardener; a curing accelerator, and a fluxing agent to form a thermally reworkable epoxy composition, and applying said thermally reworkable epoxy composition as an underfill composition.

19. The method of claim 18, wherein said cycloaliphatic epoxide is selected from the group consisting of: 3,4-epoxycyclohexyl-1-isocyanate 3,4-epoxycyclohexylmethyl carbamate; 3,4-epoxycyclohexyl-1-isocyanate 2-(3,4-epoxycyclohexyl)-2-propyl carbamate; 3,4-epoxycyclohexylmethyl 2-(1,2-epoxycyclohexyl)ethyl carbamate; phenylene-1,4-diisocyanate Bis-(3,4-epoxycyclohexylmethyl) dicarbamate; tolylene-2,4-diisocyanate Bis-(3,4-epoxycyclohexylmethyl) dicarbamate; isophorone diisocyanate Bis-(3,4-epoxycyclohexylmethyl) dicarbamate; and hexylene-1,6-diisocyanate Bis-(3,4-epoxycyclohexylmethyl) dicarbamate.

20. The method of claim 18, wherein said composition is thermally degradable at a temperature between approximately 200° C. and 250° C.

21. The method of claim 18, wherein said organic hardener is selected from the group consisting of: hexahydrophthalic anhydride, methyl hexahydrophthalic anhydride, methyl-5-norbornene-2,3-dicarboxylic anhydride, tetrahydrophthalic anhydride, methyl tetrahydrophthalic anhydride, and nadic methyl anhydride;

said curing accelerator is selected from the group consisting of: triphenylphosphine, 2-ethyl-4-methyl imidazole, 1-(2-cyanoethyl)-2-ethyl-4-methylimidazole, imidazole, 1-methylimidazole, 1-benylimidazole, 1,2-dimethylimidazole, 1-benzyl-2-methylimidazole, 4-methyl-2-phenylimidazole, benzyldimethylamine, triethylamine, pyridine, dimethylaminopyridine, 1,4-diazabicyclo[2,2,2]octane, 1,8-diazabicyclo[5,4,0]undec-7-ene, and 1,5-diazabicyclo[4,3,0]non-5-ene; and said fluxing agent is selected from the group consisting of: glycerol, glycerin, formic acid, acetic acid, tartaric acid, malic acid, citric acid and mixtures thereof.

22. The method of claim 18, wherein said organic hardener exists in a ratio of 20.0 to 80.0 parts by weight to 50 parts of said cycloaliphatic epoxide;

said curing accelerator exists in a ratio of 0.05 to 1.0 parts by weight to 50 parts of said cycloaliphatic epoxide; and said fluxing agent exists in a ratio of 1.0 to 10.0 parts by weight to 50 parts of said cycloaliphatic epoxide.

23. The method of claim 18, wherein said epoxy composition further comprises a silica filler.

24. A method of protecting a device with a cured thermally reworkable epoxy composition, the method comprising the steps of:

reacting a thermally degradable cycloaliphatic epoxide, an organic hardener; a curing accelerator, and a fluxing agent to form a thermally reworkable epoxy composition, wherein said cycloaliphatic epoxide is selected from the group consisting of: 3,4-epoxycyclohexylmethyl t-butyl carbonate and 4-epoxyethyllphenyl 2-(3-methyl-3,4-epoxycyclohexyl)-2-propyl carbonate, and applying said thermally reworkable epoxy composition as an underfill composition.

25. The method of claim 24, wherein said composition is thermally degradable at a temperature between approximately 200° C. and 250° C.

26. The method of claim 24, wherein said organic hardener is selected from the group consisting of: hexahydrophthalic anhydride, methyl hexahydrophthalic anhydride, methyl-5-norbornene-2,3-dicarboxylic anhydride, tetrahydrophthalic anhydride, methyl tetrahydrophthalic anhydride, and nadic methyl anhydride;

said curing accelerator is selected from the group consisting of: triphenylphosphine, 2-ethyl-4-methyl imidazole, 1-(2-cyanoethyl)-2-ethyl-4-methylimidazole, imidazole, 1-methylimidazole, 1-benylimidazole, 1,2-dimethylimidazole, 1-benzyl-2-methylimidazole, 4-methyl-2-phenylimidazole, benzyldimethylamine, triethylamine, pyridine, dimethylaminopyridine, 1,4-diazabicyclo[2,2,2]octane, 1,8-diazabicyclo[5,4,0]undec-7-ene, and 1,5-diazabicyclo[4,3,0]non-5-ene; and said fluxing agent is selected from the group consisting of: glycerol, glycerin, formic acid, acetic acid, tartaric acid, malic acid, citric acid and mixtures thereof.

27. The method of claim 24, wherein said organic hardener exists in a ratio of 20.0 to 80.0 parts by weight to 50 parts of said cycloaliphatic epoxide;

said curing accelerator exists in a ratio of 0.05 to 1.0 parts by weight to 50 parts of said cycloaliphatic epoxide; and said fluxing agent exists in a ratio of 1.0 to 10.0 parts by weight to 50 parts of said cycloaliphatic epoxide.

28. The method of claim 24, wherein said epoxy composition further comprises a silica filler.

* * * * *